US010184121B2

(12) United States Patent
Ortenzi et al.

(10) Patent No.: US 10,184,121 B2
(45) Date of Patent: Jan. 22, 2019

(54) METHODS FOR REMOVING VIRAL CONTAMINANTS FROM PANCREATIC EXTRACTS

(71) Applicant: Aptalis Pharma Ltd., Wicklow (IE)

(72) Inventors: Giovanni Ortenzi, Monza (IT); Luigi Ghidorsi, Milan (IT)

(73) Assignee: ALLERGAN PHARMACEUTICALS INTERNATIONAL LIMITED, Dublin (IE)

(*) Notice: Subject to any disclaimer, the term of this patent is extended or adjusted under 35 U.S.C. 154(b) by 0 days.

(21) Appl. No.: 14/744,447

(22) Filed: Jun. 19, 2015

(65) Prior Publication Data

US 2016/0122743 A1    May 5, 2016

Related U.S. Application Data

(60) Provisional application No. 62/014,337, filed on Jun. 19, 2014, provisional application No. 61/840,797, filed on Jun. 28, 2013.

(51) Int. Cl.
| *C12N 9/94* | (2006.01) |
| *C12Q 1/6806* | (2018.01) |
| *A61K 38/46* | (2006.01) |
| *A61K 38/47* | (2006.01) |
| *A61K 38/48* | (2006.01) |
| *C12Q 1/70* | (2006.01) |
| *A61K 38/00* | (2006.01) |

(52) U.S. Cl.
CPC .............. *C12N 9/94* (2013.01); *A61K 38/465* (2013.01); *A61K 38/47* (2013.01); *A61K 38/482* (2013.01); *C12Q 1/6806* (2013.01); *C12Q 1/707* (2013.01); *A61K 38/00* (2013.01); *C12Y 301/00* (2013.01); *C12Y 302/01* (2013.01); *C12Y 304/21* (2013.01)

(58) Field of Classification Search
None
See application file for complete search history.

(56) References Cited

U.S. PATENT DOCUMENTS

| 3,844,891 A | 10/1974 | Hess et al. |
| 4,079,125 A | 3/1978 | Sipos |
| 4,237,229 A | 12/1980 | Hartdegen et al. |
| 4,280,971 A | 7/1981 | Wischniewski et al. |
| 4,447,412 A | 5/1984 | Bilton |
| 4,623,624 A | 11/1986 | Schultze |
| 4,704,295 A | 11/1987 | Porter et al. |
| 4,786,505 A | 11/1988 | Lovgren et al. |
| 4,849,227 A | 7/1989 | Cho |
| 4,859,471 A | 8/1989 | Fulberth et al. |
| 5,075,231 A | 12/1991 | Moreau et al. |
| 5,225,202 A | 7/1993 | Hodges et al. |
| 5,260,074 A | 11/1993 | Sipos |
| 5,306,506 A | 4/1994 | Zema et al. |
| 5,308,832 A | 5/1994 | Garleb et al. |
| 5,324,514 A | 6/1994 | Sipos |
| 5,378,462 A | 1/1995 | Boedecker et al. |
| 5,460,812 A | 10/1995 | Sipos |
| 5,570,104 A | 10/1996 | Hayashi |
| 5,578,304 A | 11/1996 | Sipos |
| 5,665,428 A | 9/1997 | Cha et al. |
| 5,733,575 A | 3/1998 | Mehra et al. |
| 5,733,763 A | 3/1998 | Markussen et al. |
| 5,750,104 A | 5/1998 | Sipos |
| 5,861,177 A | 1/1999 | Atzl et al. |
| 5,861,291 A | 1/1999 | Abboudi et al. |
| 6,051,220 A | 4/2000 | Scharpe |
| 6,313,102 B1 | 11/2001 | Colaco et al. |
| 6,318,650 B1 | 11/2001 | Breitenbach et al. |
| 6,352,974 B1 | 3/2002 | Ghirri et al. |
| 6,426,091 B1 | 7/2002 | Okumura et al. |
| 6,607,747 B2 | 8/2003 | Ullah et al. |
| 6,777,210 B1 * | 8/2004 | Pasloske .................. C12N 9/99 435/199 |
| 6,855,336 B2 | 2/2005 | Chen et al. |
| 6,955,903 B2 | 10/2005 | Kulkarni et al. |
| 7,201,923 B1 | 4/2007 | van Lengerich |
| 7,658,918 B1 | 2/2010 | Ortenzi et al. |
| 8,071,089 B2 | 12/2011 | Schuler et al. |
| 8,221,747 B2 | 7/2012 | Ortenzi et al. |
| 8,246,950 B2 | 8/2012 | Ortenzi et al. |
| 8,293,229 B2 | 10/2012 | Ortenzi et al. |
| 8,562,978 B2 | 10/2013 | Ortenzi et al. |
| 8,562,979 B2 | 10/2013 | Ortenzi et al. |
| 8,562,980 B2 | 10/2013 | Ortenzi et al. |
| 8,562,981 B2 | 10/2013 | Ortenzi et al. |
| 8,784,884 B2 | 7/2014 | Perrett et al. |
| 2001/0024660 A1 | 9/2001 | Ullah et al. |
| 2001/0046493 A1 | 11/2001 | Margolin et al. |
| 2002/0044968 A1 | 4/2002 | van Lengerich |
| 2002/0054907 A1 | 5/2002 | Devane et al. |
| 2002/0187536 A1 | 12/2002 | Kulkarni et al. |
| 2004/0057944 A1 | 3/2004 | Galle et al. |

(Continued)

FOREIGN PATENT DOCUMENTS

| AU | 2011309763 B2 | 8/2015 |
| CA | 2263703 A1 | 8/1999 |

(Continued)

OTHER PUBLICATIONS

Solvay Pharmaceuticals "CREON®, Pancreatic Delayed-Release Capsules", Antiviral Advisory Committee, Dec. 2, 2008, p. 1-137.*

(Continued)

*Primary Examiner* — Kade Ariani
(74) *Attorney, Agent, or Firm* — Carter, DeLuca, Farrell & Schmidt, LLP

(57) ABSTRACT

Methods for screening pancrelipase for RNA virus contamination comprise removing free viral RNA from the pancrelipase, denaturing any viruses in the pancrelipase to release encapsidated RNA into the pancrelipase milieu, and detecting this released RNA. Removal of free viral RNA may comprise treating pancrelipase with RNase and DNase or precipitating the protein fraction of pancrelipase with a salt that precipitates the protein fraction while leaving nucleic acids such as RNA in solution. Pancrelipase substantially devoid of free nucleic acid is also provided.

7 Claims, 2 Drawing Sheets

Specification includes a Sequence Listing.

(56) References Cited

U.S. PATENT DOCUMENTS

| | | |
|---|---|---|
| 2004/0101562 A1 | 5/2004 | Maio |
| 2004/0121010 A1 | 6/2004 | Hirsh et al. |
| 2004/0197321 A1 | 10/2004 | Sipos et al. |
| 2004/0213847 A1 | 10/2004 | Matharu et al. |
| 2005/0019417 A1 | 1/2005 | Ko et al. |
| 2005/0158299 A1 | 7/2005 | Margolin et al. |
| 2005/0208133 A1 | 9/2005 | Tsutsumi et al. |
| 2005/0281876 A1 | 12/2005 | Li et al. |
| 2006/0121017 A1 | 6/2006 | Margolin et al. |
| 2006/0198838 A1 | 9/2006 | Fallon |
| 2007/0025977 A1 | 2/2007 | Mulberg |
| 2007/0141151 A1 | 6/2007 | Silver et al. |
| 2007/0148151 A1 | 6/2007 | Frink et al. |
| 2007/0148152 A1 | 6/2007 | Shlieout et al. |
| 2007/0190142 A1 | 8/2007 | Breitenbach et al. |
| 2008/0199448 A1 | 8/2008 | Ross et al. |
| 2008/0274174 A1 | 11/2008 | Ortenzi et al. |
| 2008/0279839 A1 | 11/2008 | Schuler et al. |
| 2008/0279953 A1 | 11/2008 | Ortenzi et al. |
| 2008/0299185 A1 | 12/2008 | Ortenzi et al. |
| 2009/0081184 A1 | 3/2009 | Margolin et al. |
| 2009/0117180 A1 | 5/2009 | Ortenzi et al. |
| 2009/0148545 A1 | 6/2009 | Falk et al. |
| 2009/0226414 A1 | 9/2009 | Tijssen et al. |
| 2009/0232789 A1 | 9/2009 | Fallon |
| 2010/0021537 A1 | 1/2010 | Ortenzi et al. |
| 2010/0239559 A1 | 9/2010 | Freedman et al. |
| 2010/0270183 A1 | 10/2010 | Ortenzi et al. |
| 2011/0064799 A1 | 3/2011 | Perrett et al. |
| 2011/0123605 A1 | 5/2011 | Ortenzi et al. |
| 2011/0123633 A1 | 5/2011 | Ortenzi et al. |
| 2011/0123634 A1 | 5/2011 | Ortenzi et al. |
| 2012/0177629 A1 | 7/2012 | Broussard et al. |
| 2012/0201875 A1 | 8/2012 | Ortenzi et al. |
| 2013/0251926 A1 | 9/2013 | Wood et al. |
| 2014/0170212 A1 | 6/2014 | Ortenzi et al. |
| 2014/0287035 A1 | 9/2014 | Perrett et al. |
| 2014/0295474 A1 | 10/2014 | Latino et al. |

FOREIGN PATENT DOCUMENTS

| | | |
|---|---|---|
| CA | 2419572 A1 | 8/2004 |
| CN | 87103560 A | 5/1988 |
| CN | 1235824 A | 11/1999 |
| CN | 1376519 A | 10/2002 |
| CN | 1489476 A | 4/2004 |
| CN | 101430279 A | 5/2009 |
| CN | 103060296 A | 4/2013 |
| DE | 2730481 A1 | 1/1978 |
| DE | 19907764 A1 | 11/1999 |
| EA | 201290985 A1 | 5/2013 |
| EP | 8780 A2 | 3/1980 |
| EP | 0035780 A1 | 9/1981 |
| EP | 0115023 A2 | 8/1984 |
| EP | 0256127 A1 | 2/1988 |
| EP | 0283442 A1 | 9/1988 |
| EP | 304332 A2 | 2/1989 |
| EP | 0576938 A1 | 1/1994 |
| EP | 0879772 A2 | 11/1998 |
| EP | 1010423 A2 | 6/2000 |
| EP | 1279402 A1 | 1/2003 |
| EP | 1335706 B1 | 4/2005 |
| EP | 1579771 A1 | 9/2005 |
| EP | 1931316 A2 | 6/2008 |
| EP | 1967211 A1 | 9/2008 |
| EP | 2079445 A2 | 7/2009 |
| EP | 2477645 A4 | 7/2012 |
| EP | 2621476 A1 | 8/2013 |
| EP | 2621476 B1 | 7/2014 |
| EP | 2754437 A2 | 7/2014 |
| EP | 2818160 A1 | 12/2014 |
| EP | 2741766 BI | 10/2015 |
| EP | 2987499 A1 | 2/2016 |
| ES | 489967 A1 | 10/1980 |
| FR | 2313916 A1 | 1/1977 |
| GB | 732951 A | 6/1955 |
| GB | 1509866 A | 5/1978 |
| GB | 2234973 A | 2/1991 |
| JP | S52-3819 A | 1/1977 |
| JP | 58-085159 | 5/1983 |
| JP | H05-38731 A | 2/1993 |
| JP | 538731 | 10/1993 |
| JP | H05-76928 B2 | 10/1993 |
| JP | 10-295374 A | 11/1998 |
| JP | H11-514088 A | 11/1999 |
| JP | H11315043 A | 11/1999 |
| JP | 2002506527 A | 2/2002 |
| JP | 2004-513645 A | 5/2004 |
| JP | 2004524838 A | 8/2004 |
| JP | 4187085 B2 | 11/2008 |
| JP | 2010519217 A | 6/2010 |
| JP | 2011093845 A | 5/2011 |
| JP | 2013530811 A | 8/2013 |
| JP | 2013534141 A | 9/2013 |
| JP | 6043929 B2 | 12/2016 |
| KR | 100395722 B1 | 11/2003 |
| KR | 20060127857 A | 12/2006 |
| KR | 100804096 B1 | 2/2008 |
| RU | 94017352 A | 7/1996 |
| RU | 2445952 C2 | 3/2012 |
| TW | 201210517 A | 3/2012 |
| WO | 8705505 A1 | 9/1987 |
| WO | 90/09428 A1 | 8/1990 |
| WO | 9009440 A1 | 8/1990 |
| WO | 90/15856 A1 | 12/1990 |
| WO | 93/07859 A1 | 4/1993 |
| WO | 93/18753 A1 | 9/1993 |
| WO | 9325669 A1 | 12/1993 |
| WO | 9600773 A1 | 1/1996 |
| WO | 9610995 A1 | 4/1996 |
| WO | 9746658 A1 | 12/1997 |
| WO | 98/01544 A1 | 1/1998 |
| WO | 97/46860 A3 | 2/1998 |
| WO | 98/58254 A1 | 12/1998 |
| WO | 01/25412 A1 | 4/2001 |
| WO | 01/70047 A1 | 9/2001 |
| WO | 0174980 A2 | 10/2001 |
| WO | 0240045 A2 | 5/2002 |
| WO | 02058735 A1 | 8/2002 |
| WO | 2004074470 A1 | 9/2004 |
| WO | 2005042012 A1 | 5/2005 |
| WO | 2005092370 A1 | 10/2005 |
| WO | 2006044529 A1 | 4/2006 |
| WO | 2007013752 A1 | 2/2007 |
| WO | 2007020259 A2 | 2/2007 |
| WO | 2007020260 A2 | 2/2007 |
| WO | 08/017659 A1 | 2/2008 |
| WO | 2008102264 A2 | 8/2008 |
| WO | 2009109856 A2 | 9/2009 |
| WO | 2011035079 A1 | 3/2011 |
| WO | 2011072069 A2 | 6/2011 |
| WO | 2011114224 A1 | 9/2011 |
| WO | 2012019186 A1 | 2/2012 |
| WO | 2012042372 A1 | 4/2012 |
| WO | 2012052853 A2 | 4/2012 |
| WO | 2013021359 A1 | 2/2013 |
| WO | 2014141121 A1 | 9/2014 |
| WO | 2015/019198 A2 | 2/2015 |
| WO | 2015/020943 A2 | 2/2015 |
| WO | 2015069677 A1 | 5/2015 |
| WO | 2015193730 A1 | 12/2015 |
| WO | 20151963730 A1 | 12/2015 |

OTHER PUBLICATIONS

Cheval et al., JCM, 2011, vol. 49, No. 9, p. 3268-3275.*

Klink et al., The Journal of Biological Chemistry, 2000, vol. 275, No. 23, p. 17463-17467.*

A. Aloulou, et al., "In Vitro Comparative Study of Three Pancreatic Enzyme Preparations: Dissolution Profiles, Active Enzyme Release and Acid Stability", Alimentary Pharmacology & Therapeutics, vol. 27, No. 3; Oct. 29, 2007; pp. 283-292.

(56) References Cited

OTHER PUBLICATIONS

A. C. Mehta, "Review of analytical methods used in the dissolution testing of pharmaceuticals", Analytical Proceedings Including Analytical Communications, vol. 31, No. 8, Jan. 1, 1994; pp. 245-248.
Alexey Khrenov: "USP Pancrelipase update", Jul. 1, 2009 and Alexey Khrenov: "USP Enzyme WOrkshop: Pancrelipase Update", Jul. 1, 2009.
"Dissolution Toolkit—Procedures for Mechanical Calibration and Performance Verification Test", USP (U.S> Pharmacopeia), Mar. 22, 2010.
New Zealand First Examination Report corresponding to New Zealand Application No. 620329, dated Oct. 16, 2014; 2 pages.
Colombian Office Action with English translation, dated Oct. 29, 2014, corresponding to Colombian Application No. 14-33910; 17 total pages including English translation.
Coutlee, et al., "Comparison of Colorimetric, Fluorescent, and Enzymatic Amplification Substrate Systems in an Enzyme Immunoassay for Detection of DNA-RNA Hybrids", Journal of Clinical Microbiology, vol. 27, No. 5, May 1989, pp. 1002-1007.
Fuhrmann, et al., "In Vivo Fluorescence Imaging of Exogenous Enzyme Activity in the Gastrointestinal Tract", Proceedings of the National Academy of Sciences of the USA, vol. 108, No. 22, May 2011; pp. 9032-9037.
Zhang, et al., "Quantitative Fluorescence Correlation Spectroscopy Reveals a 1000-Fold Increase in Lifetime of Protein Functionality", Biophysical Journal, vol. 95, Oct. 2008; pp. 3439-3446.
(Guidance for Industry) "SUPAC-MR: Modified Release Solid Oral Dosage Forms Scale-Up and Postapproval Changes: Chemistry, Manufacturing and Controls; In Vitro Dissolution Testing and In Vivo Bioequivalence Documentation" Center for Drug Evaluation and Research (CDER), Sep. 1997.
Australian Patent Examination Report No. 1, dated May 20, 2014, corresponding to Australian Application No. 2012293325; 3 pages.
Chinese Office Action dated Dec. 2, 2014 (with No English translation), corresponding to Chinese Application No. 201280040203.2; 6 pages.
Colombian Office Action (English Summary), corresponding to Colombian Application No. 13-66300; 2 pages.
Eurasian Office Action dated Jun. 30, 2014 (with English translation), corresponding to Eurasian Application No. 201390409; 5 total pages.
Handbook of Pharmaceutical Excipients, Fifth Edition, Edited by Raymond C. Rowe, et al. 4 pages.Rowe, et al., Handbook of Pharmaceutical Excipients, 4 pages.
Austrailian Patent Examination Report No. 1, dated Oct. 14, 2014, corresponding to Austrailian Application No. 2011309763; 3 pages.
European Search Report corresponding to European Application No. 14176579.2, dated Nov. 28, 2014, 4 pages.
English translation of Colombian Office Action, corresponding to Colombian Application No. 13-066300; 7 pages.
Chinese Office Action (No English translation), dated Jan. 6, 2015, corresponding to Chinese Application No. 201180055719.X; 18 pages.
Masaki Hasegawa, Direct Compression Microcrystalline Cellulose Grade 12 versus Classic Grade 102, Pharmaceutical Technology, pp. 50-60, May 2002.
Australian Patent Examination Report No. 1 corresponding to Australian Application No. 2010295494, dated Apr. 28, 2014; 3 pages.
Extended European Search Report, corresponding to European Application No. 10817867.4, dated May 26, 2014; 6 pages.
Symersky T., et al. "An Explorative Study on the Effect of Enzyme Supplementation in Patients Recovered From Acute Pancreatitis", Gastroenterology 2004; 126 (4 suppl 2): A85, Abstract 653.
Taiwanese Office Action dated Jul. 21, 2014; 6 pages.
Tawianese Search Report corresponding to Taiwanese Application No. 099131496, dated Jul. 16, 2014, 1 page.
Russian Office Action (with English Translation) corresponding to Russian Application No. 2012113253, dated Jul. 7, 2014; 8 total pages.
Colombian Office Action issued by the Colombian Patent Office on Aug. 22, 2014 (with no English translation), corresponding to Colombian Application No. 12-50658, 9 pages.
Chilean Office Action (without English Translation) dated Oct. 8, 2014, corresponding to Chilean Patent Application No. 00658-2012; 8 pages.
Japanese Notice of Rejection dated Sep. 24, 2014 (with English Translation), corresponding to Japanese Application No. 2012-529909; 6 pages.
Chinese Office Action (with No English translation), corresponding to Chinese Application No. 201080041366.3, dated Nov. 24, 2014; 3 pages.
Russian Office Action (with English translation), corresponding to Russian Application No. 2012113253, dated Nov. 25, 2014; 11 total pages.
Taiwanese Office Action (with English translation), corresponding to Taiwanese Application No. 099131496, dated Nov. 26, 2014; 10 total pages.
Pakastan Examination Report, corresponding to Pakistan Application No. 804/2010; 1 page.
English translation of Israeli Office Action, corresponding to Israeli Application No. 218656, dated Nov. 23, 2014; 2 pages.
Eurasian Office Action (with English Translation) dated Jan. 30, 2015, corresponding to Eurasian Application No. 201390409/28; 4 total pages.
Avicel-FMC, Avicel product sheet, Apr. 22, 2010.
International Search Report, and Written Opinion of the International Searching Authority, corresponding to International Application No. PCT/IB2011/002419, dated Feb. 6, 2012; 8 total pages.
Korean Office Action (with English translation), dated Nov. 24, 2014, corresponding to Korean Application No. 10-20053-7019590; 6 total pages.
Non-patent literature cited during the Appeal Procedure (universitatbonn) (D22), dated Jun. 17, 2010; 6 pages.
Letter dated Aug. 5, 2010, relating to the Appeal Procedure (Eisenfuhr Speiser); 10 pages.
Letter from Prof. Dr. Klaus-Jurgen Steffens, Rheinische Friedrich-Wilhelms-Universitat Bonn to the European Patent Office, Munich, dated Jun. 17, 2010, "Expert Opinion for Presentation at the European Patent Office"; 6 pages.
ScienceLab.com, Chemicals & Laboratory Equipment, Polyethylene Glycol 400 MSDS, Material Safety Data Sheet (D12), dated Oct. 10, 2005; 6 pages.
Kahn, et al., Bovine Pancreatic Lipase1. II. Stability and Effect of Activators and Inhibitors, Journal of Dairy Science, vol. 59, No. 5, pp. 840-846.
Worthington Biochemical Corporation, Lipase—Worthington Enzyme Manual, Triacylglycerol acylhydrolase, (D14); www.worthington-biochem.com; 2 pages.
Caelo, Macrogol 4000 Pulver, Sicherheitsdatenblatt, Seitel, von 3, (D15) dated Aug. 4, 2008; 3 pages.
Answers.com, Stir: Difinition, Synonyms of the word "Stir" from Answers.com, (D16), 9 pages.
Office Action dated Apr. 1, 2009, corresponding to U.S. Appl. No. 10/416,702, 24 pages.
Final Office Action dated Jul. 14, 2008, corresponding to U.S. Appl. No. 10/416,702, 12 pages.
Fuhrmann, Vorlesungen uber, Technische Mykologie, Verlag Gustav Fisher 1913, 80; (D19); 4 pages.
Mesh to Micron Conversion Chart—Fluideng.com, Copyright 2002—Property of TM Industrial Supply, Inc.; (D20); http://www.fluideng.com/FE/meshmicron.html; 1 page.
Australian Patent Examination Report No. 1, dated Sep. 21, 2016, corresponding to Australian Application No. 2015243026; 3 pages.
Chilean Office Action (No English translation available), dated Aug. 22, 2016, corresponding to Chilean Patent Application No. 2014-00315; 8 pages.
English translation of Israeli Office Action dated Aug. 30, 2016, corresponding to Israeli Application No. 243627; 2 pages.
Takanami et al., "Enzyme-assisted Purification of Two Phloem-limited Plant Viruses: Tobacco Necrotic Dwarf and Potato Leafroll", J. gen. Virol., vol. 44, (1979); pp. 153-159.

(56) References Cited

OTHER PUBLICATIONS

Tolin et al., "Purification and Serology of Peanut Mottle Virus", The American Phytopathological Society, vol. 73, No. 6, 1983; pp. 899-903.

Casas et al., "Detection of enterovirus and hepatitis A virus RNA in mussels (*Mytilus* spp.) by reverse transcriptase-polymerase chain reaction", Journal of Applied Microbiology, vol. 90, 2001; pp. 89-95.

Lewis et al., "Polyethylene Glycol Precipitation for Recovery of Pathogenic Viruses, Including Hepatitis A Virus and Human Rotavirus, from Oyster, Water, and Sediment Samples", Applied and Environmental Microbiology, vol. 54, No. 3, Aug. 1988; pp. 1983-1988.

Schwab et al., "Concentration and Purification of Beef Extract Mock Eluates from Water Samples for hte Detection of Enteroviruses, Hepatitis A Virus, and Norwalk Virus by Reverse Transcription-PCR", Applied and Environmental Microbiology, vol. 61, No. 2, Feb. 1995; pp. 531-537.

Eurasian Office Action (with English translation), dated May 30, 2016, corresponding to Eurasian Application No. 201590835/28; 4 total pages.

Eurasian Office Action (with English translation), dated May 30, 2016, corresponding to Eurasian Application No. 201590836/28; 4 total pages.

Eurasian Office Action (with English translation), dated Jun. 8 2016, corresponding to Eurasian Application No. 201390409/28; 4 total pages.

Chinese Office Action (No English language translation available), dated Jul. 5, 2016, corresponding to Japanese Application No. 201180055719.X; 14 pages.

Taiwanese Office Action with English tranlsation of Search Report, dated May 13, 2016, corresponding to Taiwaense Application No. 099131496; 5 total pages.

Australian Patent Examination Report No. 3, dated Jun. 28, 2016, corresponding to Australian Application No. 2014203364; 3 pages.

English translation of Chinese Third Office Action, dated Jun. 28, 2016, corresponding to Chinese Application No. 201410059861.7; 4 pages.

Korean Office Action (with English translation) dated May 16, 2016, corresponding to Korean Application No. 10-2015-7004820; 10 total pages.

English Translation of Example 3 of Priority Document Italian Patent Application No. MI2000 A 0022456; (D21); 1 page.

Summary of facts and submissions, Grounds for the Decision (Annex)—opposition, corresponding to Application No. 01 994 654.0, dated Feb. 23, 2009; 9 pages.

Interlocutory Decision in Opposition proceedings, corresponding to Application No. 01 994 654.0-2107, dated Feb. 23, 2009; 2 pages.

Druckexemplar, relating to EP1 335 706 B1, 8 pages.

Provision of the minutes in accordance with Rule 124(4) EPC, dated Feb. 23, 2009, corresponding to Application No. 01 994 654.0-2107; 12 pages.

Non-patent literature, dated Jul. 30, 2012, relating to the Appeal Procedure, (Eisenfuhr Speiser); 7 pages.

Letter from Both & Ferrari, dated Jun. 27, 2012, relating to the Appeal Procedure, 10 pages.

Non-patent literature cited during the Appeal Procedure, (Eisenfuhr Speiser), Grounds of Appeal, dated Jun. 30, 2009; 24 pages.

Letter from Botti & Ferrari, dated Sep. 18, 2009, relating to the Appeal Procedure, 15 pages.

Main Request, Claims with revisions, relating to Appeal Procedure; 1 page.

Description, relating to EP 1 335 706, relating to the Appeal Procedure; 1 page.

Main Request, Claims 1-7, relating to Appeal Procedure; 2 pages.

Royce, et al., Alternative Granulation Technique: Melt Granulation, Drug Development and Industrial Pharmacy, (D4) 22(9&10), 917-924; Copyright 1996 by Marcel Dakker, Inc.

Lombroso, "About the Destruction of the Pancreatic Enzymes by Means of Heat and the Substances that Hamper Such Action", Archivio di Farmacologia Sperimentale e Scienze Affini, Laboratory of Physiology of the R. University of Rome; 14 pages.

Novozymes—Savinase, novozymes, Rethink Tomorrow, Annex 1, A Hard-working, robust protease used to remove protein-based stains; 1 page.

Notice of Opposition to a European Patent and opposition documents related to Patent No. EP 1 335 706 B1, (Opposition file history as of Jan. 14, 2009, excluding non-duplicative, non-administrative documents; (92 total pages).

Non-patent literature dated Sep. 30, 2011, relating to the Appeal Procedure, (Eisenfuhr Speiser); 2 pages.

Non-patent literature cited during the Appeal Procedure, (universitatbonn) (D23), dated Sep. 20, 2011; 15 pages.

Non-patent literature cited during the Appeal Procedure, (One Step Ahead, Granulation and drying for all types of products), Rotolab, (D24); 8 pages.

Sincero, et al., "Detection of hepatitis A virus (HAV) in oysters (*Crassostrea gigas*)" Water Research, Elsevier, Amsterdam, NL, vol. 40, No. 5, Mar. 1, 2006; pp. 896-902.

Langeveld, et al, "Inactivated recombinant plant virus protects dogs from a lethal challenge with canine parvovirus" Vaccine, Butterworth Scientific Guildford, GB, vol. 19, No. 27, Jun. 14, 2001, pp. 3661-3670.

Singh, et al., "Canine parvovirus-like particles, novel nanomaterial for tumor targeting" Journal of Nanobiotechnology 2006, vol. 4, No. 2, dated Feb. 13, 2006; 11 pages.

Shieh, et al., "A method to detect low levels of enteric virus in contaminated oysters", Applied and environmental Microbiology, vol. 65, No. 11, Nov. 1999, pp. 4709-4714.

Bergeron, et al., Genomic Organization and Mapping of Transcription and Translation Products of the NADL-2 Strain of Porcine Parvovirus, Virology, 1993, 197(1): pp. 86-98.

Bergeron, J., Hebert, B. and Tijssen, P. (1996), Genomic Organization of the Kresse Strain of Porcine Parvovirus: Identification of the Allotropic Determinant and Comprison with Those of NADL-2 and Field Isolates, Journal of Virology 70, pp. 2508-2515.

Simpson, et al., "The Structure of Porcine Parvovirus: Comparison With Related Viruses", J. Mol. Biol., 2002, 315(5); pp. 1189-1198.

Szelei, et al., "Porcine Parvovirus". In: Kerr, et al., eds, Parvoviruses, London: Hodder Arnold; 2006; pp. 434-445.

Canaan, et al., 2004, "Interfacial Enzymology of Parvovirus Phospholipases A2", Journal of Biologizal Chemistry 279 (15), pp. 14502-14508.

Zadori, et al., 2001, "A Viral Phospholipase A2 is Required for Parvovirus Infectivity", Developmental Cell 1: pp. 291-302.

Zadori, et al., 2005, "SAT: a Late NS Protein of Porcine Parvovirus", Journal of Virology 79(20); pp. 13129-13138.

Mullendore, et al., Improved Method for the Recovery of Hepatitis A virus from oysters, Journal of Virological Methods 94, pp. 25-35 (2001).

Sair, et al., "Improved Detection of Human Enteric Viruses in Foods by RT-PCR", Journal of Virological Methods 100, pp. 57-69 (2002).

Guevremont, et al., "Development of an Extraction and Concentration Procedure and Comparison of RT-PCR Primer Systems for the Detection of Hepatitis A Virus and Norovirus GII in Green Onions", Journal of Virological Methods 134; pp. 130-135 (2006).

Hasegawa, "Microcrystalline Gellulose Grade 12 versus Classic Grade 102", Pharmacetuical Technology Europe 13 (11), pp. 28-34 (2001).

US Pharmacopeia, Chapter 786, Particle Size Distribution Estimation by Analytical Sieving, Web download, Jun. 26, 2009; 5 pages.

Gohel, "A Review of Co-Processed Directly Compressible Excipients," J. Pharm. Pharmaceutical Sciences, 8(1); pp. 76-93; (2005).

Priority Document, Italian Patent No. MI2000 A 002456, 25 pages.

International Search Report, dated Jun. 23, 2014, corresponding to International Application No. PCT/IB2014/059722; 4 pages.

Ferrie, et al., "Pancreatic Enzyme Supplementation for Patients Receiving Enteral Feeds," Techniques and Procedures, Nutrition in Clinical Practice, vol. 26, No. 3, Jun. 2011; pp. 349-351.

Chen, et al., "Enteral Nutrition Formulas: Which Formula is Right for your Adult Patient," Invited Review, Nutrition in Clinical Practice, vol. 24, No. 3, Jun./Jul. 2009; pp. 344-355.

(56) References Cited

OTHER PUBLICATIONS

International Search Report and Written Opinion of the International Searching Authority, corresponding to International Application No. PCT/US14/63984, dated Mar. 13, 2015; 10 total pages.
International Search Report and Written Opinion of the International Searching Authority, dated Mar. 13, 2015, corresponding to International Application No. PCT/US14/63984; 9 total pages.
Canadian Office Action dated Mar. 18, 2015 and Canadian Examination Search Report dated Mar. 10, 2015, corresponding to Canadian Application No. 2,677,989; 4 total pages.
International Search Report and Written Opinion of the International Searching Authority, dated Mar. 2, 2015, corresponding to International Application No. PCT/IB2014/002583; 13 total pages.
Hwang, et al., "Selective Precipitation of Proteins From Pancreatin Using Designed Antisolvents", Industrial & Engineering Chemistry Research, vol. 46, No. 12, Jun. 1, 2007; pp. 4289-4294.
International Search Report, and Written Opinion of the International Searching Authority, corresponding to International Application No. PCT/US14149569, dated Nov. 14, 2014; 8 total pages.
Queensland Government, "Tube Feeding At Home," Jan. 15, 2011, http://www.ausee.org/tube%20Feeding.pdf; 27 pages (Especially p. 13, Paragraph 3).
Wohlt, et al., "Recommendations for the Use of Medications with Continuous Enteral Nutrition," Am J Health Syst Pharm., 2009, 15 pages (Especially p. 4, Paragrah 7 and p. 5, Paragraph 1).
Singapore Search and Examination Report, dated Jan. 8, 2015, corresponding to Singapore Application No. 2012091583; 6 pages.
European Communication, dated Jan. 8, 2015, corresponding to European Patent Application No. 14176579.2; 2 pages.
International Search Report and Written Opinion of the International Searching Authority dated Nov. 20, 2015, corresponding to International Application No. PCT/IB2015/001237; 17 total pages.
Schielke et al., "Thermal Stability of Hepatitis E. Virus Assessed by a Molecular Biological Approach," Virology Journal, Biomed Central, vol. 8, No. 1, Oct. 31, 2011; 9 pages.
International Written Opinion of the International Searching Authority and International Search Report dated Jan. 19, 2010, corresponding to International Application No. PCT/IB2009/000472; 7 total pages.
International Preliminary Report on Patentability and Written Opinion of the International Searching Authority, dated Jan. 26, 2016, corresponding to International Application No. PCT/IB2014/002583; 10 total pages.
European Search Report dated Jan. 22, 2016, corresponding to European Application No. 15178147.3; 9 pages.
Communication of the Board of Appeal, corresponding to Appeal No. T2255/12-3.3.07, dated Mar. 7, 2016; 11 pages.
Non-Patent Literature document—"Oppoistion against European Patent No. 1 931 316 in the anme of Abbott Products GmbH," correspnding to Appeal No. T2255/12-3.3.07, (letter from Both & Ferrari, to the European Patent Office), dated May 13, 2013; 9 pages.
Non-Patent Literature document—"Notice of Appeal against the decision revoking the patent further to opposition proceedings," (from Cabinet Beau de Lomenie to the European Patent Office), corresponding to European Patent No. 1 931 316, dated Oct. 26, 2012; 1 page.
Non-Patent Literature document—"Grounds of Appeal", (from Cabinet Beau de Lomenie to the European Patent Office), corresponding to European Patent No. 1 931 316, dated Jan. 2, 2013; 10 pages.
Non-Patent Literature document—"Decision revoking the European Patent," issued by the European Patent Office, corresponding to European Patent No. 1 931 316, dated Sep. 5, 2012; 14 pages.
Non-Patent Literature document—"Persons attending oral proceedings on patentee's side," (from Cabinet Beau de Lomenie to the European Patent Office), corresponding to European Patet No. 1 931 316, dated May 2, 2012; 1 page.
Non-Patent Literature document—"Submission in opposition proceedings," issued by the European Patent Office, corresponding to European Patent No. 1 931 316, dated May 2, 2012; 1 page.

Non-Patent Literature document—"Reply to summons to attend oral proceedings; filing of new main claim request," (from Cabinet Beau de Lomenie to the European Patent Office), corresponding to European Patent No. 1 931 316, dated Feb. 23, 2012; 2 pages.
Non-Patent Literature document—"Submission in opposition proceedings," issued by the European Patent Office, corresponding to European Patent No. 1 931 316, dated Feb. 23, 2012; 2 pages.
Non-Patent Literature document—Letter from Europatent to European Patent Office, corresponding to European Patent No. 1 931 316, dated Feb. 6, 2012; 1 page.
Thoma et al., "Influence of aqueous coatings on the stability of enteric coated pellets and tablets," European Journal of Pharmaceutics and Biopharmaceutics, Elsevier, (D11), vol. 47(1), (1999); pp. 39-50.
Non-Patent Literature document—"Submission in opposition proceedings," issued by the European Patent Office, corresponding to European Patent No. 1 931 316, dated Jan. 11, 2012; 2 pages.
Non-Patent Literature document—"Inquiry concerning summons to oral proceedings," (from Cabinet Beau de Lomenie to the European Patent Office), corresponding to European Patent No. 1 931 316, dated Jan. 11, 2012; 1 page.
Non-Patent Literature document—"Brief Communication, Communication pursuant to Article 1(2) of the decision of the President of the EPO dated Jul. 12, 2007 concerning the filing of authorisations and Communication of amended entries concerning the representative," dated Sep. 20, 2011, issued by the European Patent Office, corresponding to European Patent No. 1 931 316; 3 total pages.
Non-Patent Literature document—"Notice of Opposition Filed by Eurand S.p.A.," (from Abbott Products GmbH), corresponding to European Patent No. 1 931 316, dated Jun. 7, 2011; 6 pages.
Naftifine HCl—MSDS—Material Safety Data Sheet, created Jun. 23, 2004; http://pharmacycode.com/msds/Naftifine_HCl; 4 pages.
Australian Patent Examination Report No. 2, dated Feb. 25, 2016, corresponding to Australian Application No. 2014203364; 5 pages.
Egyptian Office Action (No English translation available), dated Mar. 20, 2016, corresponding to Egyptian Application No. PCT 1257/2009; 5 pages.
Japanese Office Action (with English translation), dated Mar. 1, 2016, corresponding to Japanese Application No. 2014-524476; 5 total pages.
Chinese Office Action (No English translation available), dated Feb. 15, 2016, corresponding to Chinese Application No. 201180055719. X; 14 pages.
"Polymer Science in Pharmaceutics", Junmin Zheng, China Medical Science Press, pp. 113-114, Jan. 31, 2009)—Article Unavailable.
Mexican Office Action (No English translation available), corresponding to Mexican Application No. MX/a/2013/003627, dated Mar. 10, 2016; 2 pages.
International Preliminary Report on Patentability and Written Opinion of the International Searching Authority, dated Feb. 9, 2016, corresponding to International Application No. PCT/US2014/049569; 7 total pages.
Korean Notice of Final Rejection (with English translation), dated Dec. 28, 2015, corresponding to Korean Application No. 10-2015-7004820; 8 total pages.
Canadian Office Action dated Mar. 16, 2016, corresponding to Canadian Application No. 2,677,989; 4 pages.
Malaysian Office Action dated Mar. 31, 2016, corresponding to Malaysian Application No. PI 2012001215; 3 pages.
Non-Patent Literature document—"Notice of Opposition against the European Patent EP-B-1 931 316", (letter from Botti & Ferrari to the European Patent Office), dated Nov. 15, 2010, 12 pages.
Colombian Office Action (No English translation available), dated Feb. 19, 2016, corresponding to Colombian Application No. 14-026502; 8 pages.
Non-Patent Literature Document—"Aqueous Coating—Aquacoat ECD," FMC Biopolymer; 12 pages.
Non-Patent Literature document—"Brief Communication," dated Feb. 10, 2011, issued by the European Patent Office, corresponding to European Application No. 067782409 (European Patent No. 1 931 316); 1 page.

(56) References Cited

OTHER PUBLICATIONS

Non-Patent Literature document—"Vollmacht Authorisation Pouvoir," (German document—Power of Representation before the EPO for European Patent No. 1 931 316, dated Sep. 13, 2011; 3 total pages.
Non-Patent Literature document—"Claims—First Auxiliary Request" and "Claims—Second Auxiliary Request," dated Sep. 2011, corresponding to Opposition Proceedings of European Patent No. 1 931 316; 12 total pages.
Non-Patent Literature document—"Brief Communication—Main Request", dated Jun. 17, 2011, corresponding to European Patent No. 1 931 316; 8 total pages.
Non-Patent Literature document—"Notice of Opposition to a European Patent," dated Nov. 15, 2010, corresponding to European Patent No. 1 931 316; 5 pages.
Non-Patent Literature document—"Decision to grant a European patent pursuant to Article 97(1) EPC," corresponding to European Patent No. 1 931 316, dated Jan 21. 2010; 2 pages.
Non-Patent Literature document—"A2PAMPHLET," related to WO 2007/020259 (PCT/EP2006/065311), printed on May 19, 2008; 29 total pages.
Non-Patent Literature document—"Claims (EP 06 778 240)," printed Sep. 25, 2008; 12 total pages.
Israeli Office Action (No English translation available), dated Apr. 3, 2016, corresponding to Israeli Application No. 218656; 2 pages.
Sankalia M.G. et al., "Papain Entrapment in Alginate Beads for Stability Improvement and Site-Specific Delivery: Physicochemical Characterization and Factorial Optimization Using Neural Network Modeling," AAPS PharmSciTech., 2005; vol. 6, No. 2, Article 31; pp. E209-E222.
Scheich C. et al., "An Automated In Vitro Protein Folding Screen Applied to a Human Dynactin Subunit," Protein Science, 2004, vol. 13; pp. 370-380.
Miller D.A. et al., "Evaluation of the USP Dissolution Test Method A for Enteric-Coated Articles by Planar Laser-Induced Fluorescence," International Journal of Pharmaceuticals, 2007, vol. 330; pp. 61-72.
Ramos et al., "Time-Resolved Fluorescence Allows Selective Monitoring of Trp30 Environmental Changes in the Seven-Trp-Containing Human Pancreatic Lipase," Biochemistry 2003, vol. 42; pp. 12488-12496.
Chinese First Office Action and Search Report (English translations), dated Apr. 3, 2015, corresponding to Chinese Patent Application No. 201410059861.7; 23 total pages.
Israeli Office Action dated May 10, 2015 (No English translation), corresponding to Israeli Patent Application No. 200407; 2 pages.
European extended Search Report, dated Jun. 2, 2015, corresponding to European Patent Application No. 14150794.7; 10 pages.
Japanese Office Action (with English translation), dated May 12, 2015, corresponding to Japanese Patent Application No. 2013-530811; 8 total pages.
Canadian Office Action dated Jul. 3, 2015, corresponding to Canadian Patent Application No. 2,774,269; 4 pages.
Japanese Final Office Action (No English translation), dated Jul. 7, 2015, corresponding to Japanese Patent Application No. 2012-529909; 3 pages.
Chilean Office Action (without English Translation) dated Jul. 22, 2015, corresponding to Chilean Patent Application No. 00658-2012; 8 pages.
Communication of a Notice of Oppoistion to a European Patent Application and opposition documents related to Patent Application No. EP 117885223.3, dated Aug. 5, 2015 (678 total pages).
Arbocel Product Sheet.
Wikipedia Search Result for Mehl (No English translation).
U.S. Appl. No. 61/389,037, filed Oct. 1, 2010 (prosecution history).
Chinese Office Action (No English translation available), dated Jul. 28, 2015, corresponding to Chinese Patent Application No. 201180055719.X; 13 pages.
Russian Office Action (with English translation), dated Jun. 15, 2015, corresponding to Russian Patent Appplication No. 2014104591/15; 10 total pages.

European Communication dated Jul. 6, 2015, corresponding to European patent application No. 14150794.7; 2 pages.
Korean Notice of Preliminary Rejection (with English translation), dated Jun. 12, 2015, corresponding to Korean patent application No. 10-2015-7004820; 16 total pages.
Australian Patent Examination Report No. 1, dated Jul. 6, 2015, corresponding to Australian Patent Application No. 2014203364; 4 pages.
Japanese Office Action (No English translation), dated May 12, 2015, corresponding to Japanese Patent Application No. 2013-530811; 3 pages.
Canadian Office Action and Examination Search Report dated Sep. 3, 2015, corresponding to Canadian Patent Application No. 2,677,989; 4 total apges.
Japanese Decision of Rejection (with English translation) dated Sep. 25, 2015, corresponding to Japanese Applcation No. 2013-265143; 9 total pages.
English translation of Chinese Second Office Action dated Dec. 21, 2015, corresponding to Chinese Application No. 2014100598611; 5 pages.
Taiwanese Office Action (with English translation), dated Nov. 3, 2015, corresponding to Taiwanese Application No. 102138934; 16 total pages.
International Preliminary Report on Patentability and Written Opinion of the International Searching Authoirty, corresponding to International Application No. PCT/IB2014/059722, dated Sep. 15, 2015; 9 Pages.
Australian Patent Examination Report 1, dated Sep. 15, 2015, corresponding to Australian Patent Application No. 2014253526; 3 pages.
Eurasian Search Report (with English translation) issued by the EUrasian Patent Organization (EAPO) dated Sep. 16, 2015, corresponding to Eurasian Patent Application No. 201590836; 4 total pages.
Eurasian Search Report (with English translation) issued by the EUrasian Patent Organization (EAPO) dated Sep. 16, 2015, corresponding to Eurasian Patent Application No. 201590835; 4 total pages.
Ukrainian Office Action (with English Translation) dated Sep. 23, 2015, corresponding to Ukraine Application No. a 2013 03847; 11 total pages.
Colombian Office Action (No English Translation Available), dated Sep. 30, 2015, corresponding to Colombian Application No. 14-33910; 11 pages.
Eurasian Office Action (With English Translation) dated Oct. 30, 2015, correpsonding to Eurasian Application No. 201390409/28; 4 total pages.
English translation of Israeli Office Action dated Jan. 11, 2016, corresponding to Israeli Patent Application No. 225504; 3 pages.
Russian Office Action (with English translation), dated Oct. 29, 2015, corresponding to Russian Application No. 2014104591; 7 total pages.
English translation of Israeli Office Action, dated Sep. 29, 2016, corresponding to Israeli Application No. 241540; 2 pages.
European Communication dated Jan. 2, 2017, corresponding to European Application No. 14 717 867.7; 5 pages.
European Communication and Supplemental Partial European Search Report, dated Nov. 14, 2016, corresponding to European Application No. 14859866.7, 9 pages.
European Communication dated Sep. 29, 2016, corresponding to European Application No. 10 817 867.4; 3 pages.
Korean Office Action (with English translation), dated Nov. 11, 2016, corresponding to Korean Application No. 10-2012-7009516; 12 total pages.
Israeli Office Action dated Jan. 16, 2017, corresponding to Israeli Application No. 218656; 2 pages.
Israeli Office Action dated Jan. 17, 2017, corresponding to Israeli Application No. 245875; 2 pages.
Mexican Office Action (No English translation available), dated Aug. 19, 2016 (received Sep. 8, 2016), corresponding to Mexican Application No. MX/a/2013/003627; 3 pages.

(56) References Cited

OTHER PUBLICATIONS

Eurasian Office Action (with English translation), dated Dec. 19, 2016, corresponding to Eurasian Application No. 201390409/28; 4 total pages.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, (1997); pp. 498-506.
Handbook of Pharmaceutical Excipients, Fifth Edition, Edited by Raymond C. Rowe, et al. (Aug. 2005) 4 pages.
Kahn, et al., Bovine Pancreatic Lipase1. II. Stability and Effect of Activators and Inhibitors, Journal of Dairy Science, vol. 59, No. 5, Apr. 1975; pp. 840-846
Description, relating to EP 1 335 706, paragraphs [0022] through [0036], relating to the Appeal Procedure (E8); 1 page.
Arbocel Product Sheet, J. Rettenmaier & Bohne Gmbh & Co. (JRS); 1 page, 2017.
Novozymes—Savinase, novozymes, Rethink Tomorrow, Annex 1, A Hard-working, robust protease used to remove protein-based stains; Copyright 2008 Novozymes; 1 page.
Non-patent literature cited during the Appeal Procedure, (One Step Ahead, Granulation and drying for all types of products), Rotolab, (D24); Jun. 28, 2012; 8 pages.
Wikipedia Search Result for Mehl (Flour in English) (English translation also attached); printed from www.wikipedia.com Feb. 2, 2017; 18 total pages.
European Communication dated Mar. 2, 2017, corresponding to European Application No. 15 178 147.3; 6 pages.
European Extended Search Report dated Feb. 15, 2017, corresponding to European Application No. 14833670.4; 9 pages.
"Ensure Plus HN", ip.com Journal, ip.com Inc., West Henrietta, NY, US, Feb. 9, 2002 (This document completes the disclosure of US2012/177629 with respect to the composition of the product Ensure Plus); 1 page.
Sackman et al., "Does Mixing Pancreatic Enzyme Microspheres (Pancrease) with Food Damage the Enteric Coating?" Journal of Pediatric Gastroenterology and Nutrition, Jan. 1, 1982; pp. 333-335.
Shlieout et al., "Administration of CREON Pancrelipase Pellets via Gastrostomy Tube is Feasible with no Loss of Gastrict Resistance or Lipase Activity—An In Vitro Study", Clinical Drug Investigation, vol. 31, No. 7, Jan. 1, 2011; pp. e1-e7.
Canadian Office Action and Examination Search Report, dated Nov. 18, 2016, corresponding to Canadian Application No. 2,677,989; 3 total pages.
English translation of Chinese Office Action dated Jan. 20, 2017, corresponding to Chinese Application No. 201410059861.7; 4 total pages.
Australian Examination Report No. 1, dated Feb. 8, 2017, corresponding to Australian Application No. 2016204414; 5 pages.
Nakamura et al., "Effects of High-Lipase Pancreatin on Fecal Fat, Neutral Sterol, Bile Acid, and Short-Chain Fatty Acid Excretion in Patients with Pancreatic Insufficiency Resulting from Chronic Pancreatitis," International Journal of Pancreatology, Feb. 1998; vol. 23, No. 1; pp. 63-70.
G. J. Peschke, "Active Components and Galenic Aspects of Enzyme Preparations," Pancreatic Enzymes in Health and Disease, Springer-Verlag Berlin Heidelberg, 1991; pp. 55-64.
Japanese Office Action (no English translation available), dated Jul. 4, 2017, corresponding to Japanese Application No. 2016-196831.
Canadian Office Action and Examination Search Report, dated Aug. 16, 2017, corresponding to Canadian Application No. 2,812,862; 4 total pages.
Eurasian Office Action (with English Translation) dated Sep. 6, 2017, corresponding to Eurasian Application No. 201590835/28; 2 total pages.
Eurasian Office Action (with English Translation) dated Sep. 6, 2017, corresponding to Eurasian Application No. 201590836/28; 2 total pages.
European Communication dated Apr. 11, 2017, corresponding to Eurpoean Application No. 14859866.7; 1 page.
European Search Report dated Mar. 24, 2017, corresponding to European Application No. 14859866.7; 21 total pages.
Australian Examination Report, dated Apr. 10, 2017, corresponding to Australian Application No. 2016216662; 3 pages.
European Communication dated May 19, 2017, corresponding to European Application No. 10817867.4; 3 pages.
European Communication dated Aug. 2, 2017, corresponding to European Application No. 15 178 147.3; 8 pages.
Opekun, Jr. et al., "Lack of dose-response with Pancrease MT for the treatement of exocrine pancreatic insufficiency in adults," Blackwell Science Ltd., Aliment Pharmacol Ther (1997), vol. 11; pp. 981-986.
"Clinical Pharmacology and Biopharmaceutics Revew(s)", Center for Drug Evaluation and Research, Apr. 23, 2010, Application No. 022523Orig1s000; 37 pages—Retrieved from the Internet: https:www.accessdata.fda.gov/drugsatfda_docs/nda/2010/022523orig1s000clinpharmr.pdf.
"Pancrease MT Capsules", Aug. 2005, Drug Reference Encyclopedia; 7 pages—Retrieved from the Internet: https://theodora.com/drugs/pancrease_mt_capsules_mcneil_consumer.html.
European Communication dated Sep. 15, 2017, corresponding to European Application No. 14 815 008.9; 7 total pages.
Argentine Office Action dated Mar. 31, 2017, corresponding to Argentine Application No. P080100693; 6 pages (No English language translation available).
Taiwanese Office Action (with English translation), dated Feb. 16, 2017, corresponding to Taiwanese Aplication No. 102138934; 5 total pages.
Examination Report and Search Report issued by the Korean Intellectual Property Office dated Jul. 3, 2017, corresponding to AE Application No. UAE/P/0743/2009; 13 total pages.
Korean Office Action (with English Translation) dated Sep. 5, 2017, corresponding to Korean Application No. 10-2013-7010970; 12 total pages.
European Examination Report dated Dec. 4, 2018, corresponding to European Application No. 14 859 866.7; 5 pages.
Singapore Search Report and Examination Report dated Feb. 9, 2018, corresponding to Singapore Application No. 10201405791X; 6 total pages.
Dominguez-Munoz et al., "Effect of Oral Pancreatic Enzyme Administration on Digestive Function in Healthy Subjects: Comparison Between Two Enzyme Preparations," Aliment Pharmacol Ther. 11, vol. 13, No. 2, Apr. 1, 1997; pp. 403-408.
Japanese Office Action dated Dec. 12, 2017, corresponding to Japanese Application No. 2016-196831; 3 total pages.
English translation of Korean Office Action dated Mar. 29, 2018, corresponding to Korean Application No. 10-2013-7010970; 3 pages.
Russian Office Action and Search Report (with English translation) dated Feb. 16, 2018, corresponding to Russian Application No. 2016103606; 13 total pages.
Russian Decision to Grant (with English translation), dated Feb. 27, 2018, corresponding to Russian Application No. 2015138541/15; 12 total pages.
Russian Office Action and Search Report (with English translation), dated Nov. 9, 2017, corresponding to Russian Application No. 2015138541/15; 11 total pages.
Australian Examination Report dated Jan. 8, 2018, corresponding to Australian Application No. 2014229330; 4 pages.
English translation of Japanese Office Action dated Feb. 27, 2018, corresponding to Japanese Application No. 2016-528615; 13 pages.
Korean Notice of Allowance (with English translation), dated Dec. 6, 2017, corresponding to Korean Application No. 10-2015-7004820; 3 pages.
Australian Examination Report dated Oct. 11, 2017, corresponding to Australian Application No. 2016204414; 3 pages.
Singapore Notice of Eligibility for Grant, including Examination Report and Search Report, dated Feb. 27, 2018, corresponding to Singapore Application No. 10201405791X; 9 total pages.
Indian Examination Report dated Dec. 29, 2017, corresponding to Indian Application No. 3078/CHENP/2013; 5 pages.
Korean Office Final rejection (with English translation), dated Mar. 29, 2018, corresponding to counterpart Japanese Application No. 10-2013-7010970; 6 total pages.

(56) References Cited

OTHER PUBLICATIONS

Russian Office Action and Search Report (with English translation) dated Nov. 9, 2017, corresponding to Russian Application No. 2015138541; 11 total pegs.
English Translation of Japanese Office Action dated Nov. 6, 2017, corresponding to Japanese Application No. 2015-562502; 5 pages.
Chinese Office Action dated Jun. 2, 2017, corresponding to Chinese Application No. Jun. 2, 2017; 7 pages.
Japanese Office Action (wish English translation), dated Nov. 14, 2017, corresponding to Japanese Application No. 2015-562502; 10 total pages.
English translation of Russian Office Action and Search Report dated Feb. 16, 2018, corresponding to Russian Application No. 2016103606; 6 total pages.
Japanese Office Action (with English translation) dated Mar. 27, 2018, corresponding to Japanese Application No. 2016-53356; 10 total pages.
Eiyogaku Zasshi (Nahomi Imaeda) "Food Composition Table for Retort-Packaged Baby Foods", Department of Food Science and Nutrition, Faculty of Human Life and Environmental Sciences, Nagoya Women's University, Jpn. J. Nutr. Diet, 2008, vol. 66, No. 5; pp. 255-262.
Ensure Plus milkshake style, 2015 (online), [search Mar. 13, 2018], Retrieved from the internet, URL: http://1www.abbottnutrition.ie/content/datasheets/Ensure_Plus_datasheet_January_2015_pdf.
Canadian Office Action and Examination Search Report, dated Apr. 27, 2018 corresponding to counterpart Canadian Application No. 2,843,556; 6 total pages.
European Communication dated Mar. 5, 2018, corresponding to counterpart European Application No. 15 750 805.2; 3 pages.
Solvay Pharmaceuticals: "Solvay Pharmaceuticals Creon (Pancrelipase Delayed-Release Capsules) Antiviral Drugs Advisory Committee, Dec. 2, 2008, Open Session (Appendices 1 and 2 for Closed Session under seperate cover) Available for Public Disclosure Without Redaction"; Dec. 2, 2008 (XP055454900); Retrivede from the Internet: https://www.fda.gov/ohrms/dockets/ac/08/briefing/2008-4402b1-03-SOLVAY.pdf; 137 pages.
International Search Report, Written Opinion and International Preliminary Report on Patentability based on International Application No. PCT/IB2008/000770, dated Jun. 3, 2009; 13 pages.
Krishnamurty et al., "Delayed release pancrelipase for treatment of pancreatic exocrine insufficiency associated with chronic pancreatitis," Therapeutics and Clinical Risk Management, (May 2009) pp. 507-520.
Drugs@FDA Glossary of Terms, printed Nov. 20, 2009; http://www.fda.gov/Drugs/InformationonDrugs/ucm079436.htm; 7 pages.
Guidance for Industry #191, Changes to Approved NADAs—New NADAs vs. Category II Supplemental NADAs, Final Guidance, U.S. Department of Health and Human Services, Food and Drug Administration, Center for Veterinary Medicine, Released Nov. 19, 2009: 25 pages.
Singapore Written Opinion, corresponding to Singapore Patent Application No. 200905385-1, issued by the Austrian Patent Office dated Dec. 16, 2010; 6 pages.
Hageman, "The Role of Moisture in Protein Stability," Drug Development and Industrial Pharmacy, vol. 14, No. 14, (1988); pp. 2047-2070.
Maul and Schmidt, "Influence of different-shaped pigments on bisacodyl release from Eudragit L 30 D," International Journal of Pharmacetuics, vol. 118, No. 1, May 1, 1995; pp. 103-112.
Maul and Schmidt, "Influence of different-shaped pigments and plasticizers on theophylline release from Eudragit RS30D and Aquacoat ECD30 coated pellets," S.T.P. Pharma Sciences, vol. 7, No. 6, pp. 498-506.
Felton and McGinity, "Influence of Insoluble Excipients on Film Coating Systems," Drug Development and Industrial Pharmacy, vol. 28, No. 3; pp. 225-243.
Parker et al., "Effects of Solids-Loading on Moisture Permeability Coefficients of Free Films," Journal of Pharmaceutical Sciences, vol. 63, No. 1 (Jan. 1974); pp. 119-125.
Thoma and Bechtold, "Influence of aqueous coatings on the stability of enteric coated pellets and tablets," European Journal of Pharmaceutics and Biopharmaceutics, vol. 47, (1999), pp. 39-50.
Nordmark pancreatin brochure, Products all over the World, (publication year unknown); 7 pages.
Australian First Examination Report, dated Mar. 23, 2012, corresponding to Australian Patent Application No. 2008218595; 2 pages.
English Translation of Second Chinese Office Action, dated Apr. 12, 2012, corresponding to Chinese Patent Application No. 200880012762.6; 5 pages.
European Communication, dated Jan. 3, 2012, corresponding to European Patent Application No. 08719392.6; 7 pages.
European Communication, dated Aug. 1, 2012, corresponding to European Patent Application No. 08719392.6; 7 pages.
New Zealand First Examination Report, dated Aug. 26, 2010, corresponding to New Zealand Patent Application No. 579047; 3 pages.
New Zealand Second Examination Report, dated Dec. 15, 2011, corresponding to New Zealand Patent Application No. 579047; 2 pages.
New Zealand First Examination Report, dated Feb. 29, 2012, corresponding to New Zealand Patent Application No. 598477; 1 page.
Singapore Second Written Opinion, dated Nov. 22, 2011, corresponding to Singapore Patent Application No. 200905385-1; 6 pages.
U.S. Office Action, dated Mar. 20, 2012, corresponding to U.S. Appl. No. 12/034,480; 7 pages.
U.S. Office Action, dated Oct. 14, 2011, corresponding to U.S. Appl. No. 12/034,480; 15 pages.Office Action for U.S. Appl. No. 12/034,480, dated Oct. 14, 2011, 15 pages.
U.S. Office Action, dated Mar. 19, 2012, corresponding to U.S. Appl. No. 12/034,488; 8 pages.
U.S. Office Action, dated Oct. 25, 2011, corresponding to U.S. Appl. No. 12/034,488; 14 pages.
U.S. Office Action, dated Jan. 4, 2012, corresponding to U.S. Appl. No. 12/034,491; 7 pages.
U.S. Office Action, dated Jun. 23, 2011, corresponding to U.S. Appl. No. 12/034,491; 7 pages.
U.S. Office Action, dated Jun. 26, 2012, corresponding to U.S. Appl. No. 13/019,844; 15 pages.
U.S. Office Action, dated May 24, 2012, corresponding to U.S. Appl. No. 13/019,856; 9 pages.
U.S. Office Action, dated May 23, 2012, corresponding to U.S. Appl. No. 13/019,860; 5 pages.
U.S. Office Action, dated Jul. 2, 2012, corresponding to U.S. Appl. No. 12/832,596; 11 pages.
International Search Report and Written Opinion, dated Oct. 22, 2012, corresponding to International Application No. PCT/US2010/049203; 6 pages.
Canadian Office Action, dated May 6, 2014, corresponding to Canadian Application No. 2,677,989, 2 pages.
Colombian Office Action (with No English translation), dated May 26, 2014, corresponding to Colombian Application No. 09.101.677, 4 pages.
Costa Rica Preliminary Technical Report—1st Phase, corresponding to Costa Rica Application No. 11031, dated Jun. 12, 2014; 11 total pages.
European Communication dated Apr. 8, 2014, corresponding to European Application No. 08 719 392.6, 6 pages.
Indian Office Action, dated Oct. 17, 2014, corresponding to Indian Application No. 5854/DELNP/2009; 4 pages.
Japanese Decision of Rejection and Decision of Dismissal of Amendment (with English translations), dated Aug. 25, 2014, corresponding to Japanese Application No. 2009-549868; 9 total pages.
Singapore Search Report, dated Apr. 7, 2014 and Singapore Written Opinion, dated Apr. 28, 2014, corresponding to Singapore Application No. 2012091583; 11 total pages.
Japanese Office Action (with English translation), dated Jan. 19, 2015, corresponding to Japanese Application No. 2013-265143, 11 total pages.

(56) References Cited

OTHER PUBLICATIONS

Taiwanese Office Action and Search Report (with English translation, dated Oct. 3, 2014, corresponding to Taiwanese Application No. 102138934; 10 total pages.
Colombian Office Action (with No English translation), dated Sep. 23, 2014, corresponding to Colombian Application No. 14.026.502, 4 pages.
The Decision of the Enlarged Board of Appeal, dated Nov. 22, 2013, 18 pages.
The Minutes of the Oral Proceedings of Nov. 22, 2013, 6 pages.
Communication from the Enlarged Board of Appeal pursuant to Articles 13 and 14(2) RPEBA, dated Sep. 17, 2013; 6 pages.
Letter from Botti & Ferrari regarding a Petition for Review of Decision T0977/09-3.3.02, European Patent No. 1 335 706 in the name of Aptalis Pharma S.r.l., dated May 15, 2013; 12 pages.
Termination of Opposition Proceedings of Patent No. 01994654.0/1456 / 1335706 with Revocation of the Patent, dated Mar. 14, 2013; 2 pages.
Decision dated Nov. 30, 2012; 28 pages.
The Minutes of the Oral Proceedings of Nov. 30, 2012; 18 pages.
International Search Report, International Preliminary Report on Patentability and Written Opinion of the International Searching Authority, corresponding to International Application No. PCT/IB2012/054050, dated Nov. 14, 2012; 11 total pages.

\* cited by examiner

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: Hepatitis E Primer ORF Sense

<400> SEQUENCE: 1
gacagaattr atttcgtcgg ctgg                                      24

<210> SEQ ID NO 2
<211> LENGTH: 25
<212> TYPE: DNA
<213> ORGANISM: Artificial Sequence
<220> FEATURE:
<223> OTHER INFORMATION: Hepatitis E ORF2 Antisense

<400> SEQUENCE: 2
cttgttcrtg ytggttrtca taatc                                     25
```

METHODS FOR REMOVING VIRAL CONTAMINANTS FROM PANCREATIC EXTRACTS

CROSS-RELATED APPLICATION

This application claims the benefit under 35 USC § 119(e) of U.S. Provisional Patent Application Ser. No. 62/014,337 filed Jun. 19, 2014, the disclosure of which is herein incorporated by reference in its entirety for all purposes.

FIELD OF THE INVENTION

The present invention relates generally to the field of pharmaceutical quality assurance. More particularly, the invention relates to methods for significantly reducing false positive results in the screening of pancreatic extracts for the presence of RNA viruses, such as the hepatitis E virus (HEV).

BACKGROUND OF THE INVENTION

Biologic drugs pose several unique manufacturing and regulatory challenges due to their intrinsic and complex profile. They have a high level of structural complexity and heterogeneity, are produced in living systems or supplemented with reagents derived from living systems, and consequently have a complex purity/impurity profile that poses unique analytical challenges, particularly from a quality and safety perspective.

Ensuring the safety of biologic drugs is important. Contamination, including the presence of pathogenic microorganisms, such as viruses, may cause serious illness or even death in certain patients to whom such drugs are administered. Indeed, regulatory approval of such drugs depends, in part, on eliminating, or at least reducing the levels of pathogenic microorganisms in the drug to acceptable levels. After removal of microorganisms from the biologic drugs, the drugs are screened to confirm the removal of the microorganisms.

In contrast to cellular microorganisms such as bacteria, which can be multiplied prior to their detection, most virus particles need to be directly detected in the respective sample. Generally, the presence of virus is detected by way of PCR-based amplification and detection of viral DNA or RNA. It is, thus, important to have sensitive detection methods available for screening and detection of viral contaminants. Current detection methods, while sensitive, nevertheless still suffer from the drawback of producing both false negative and false positive results. The former is problematic insofar as it may result in a patient receiving a contaminated drug, and the latter is problematic insofar as it may result in a good batch of drug being destroyed or subjected to further expensive processing.

Pancrelipase is a biologic drug. This drug is a porcine-derived mixture of digestive enzymes, including pancreatic amylase, pancreatic lipase, and pancreatic proteases. It is used to enable patients with pancreatic insufficiency to better digest their food. Pancrelipase is prepared from porcine pancreases and, comprises, in addition to the amylase, lipase, and proteases, various types of other enzymes, salts, nucleic acids and carbohydrates. Pancrelipase is highly enzymatically active, having been prepared for this specific property, and in this respect, it is unlike other biological matrices and biological drugs. Being prepared from a biological source, the precursor of the pancrelipase end product may contain human pathogens such as viruses, which must be removed.

The methods used to extract the digestive enzymes from the pancreas glands, to form pancrelipase, result in a reduction in viral number and in viral infectivity through destruction of the viral envelope or capsid. Some viruses are able to survive the processing steps, although infectivity of such viruses may be degraded. Examples of such viruses include the Hepatitis E Virus (HEV).

To establish that pancrelipase is HEV-free, samples are subject to PCR-based amplification and detection of HEV RNA. The inference of the presence of virus, and therefore viral contamination of the pancrelipase, is made through the detection of base sequences specific to the virus. Viral RNA may be present in free form (absent any viral capsid) as an artifact of the pancrelipase production processes, or may be present encapsidated or intact as contaminating viruses. The former is not generally grounds for concern, although the latter indicates viral contamination. Unfortunately, however, current amplification and detection methods do not distinguish between free and encapsidated or intact viral RNA. Pancrelipase is a very difficult product on which to perform analyses of biological constituents, due to the enzymes thereof interfering with analyses, for example by the enzymes reacting/converting biological constituents of the sample to be tested or components used to effect the analysis. Therefore, detection methods and analytical techniques need to be specifically tailored for use with pancrelipase samples.

Before encapsidated RNA can be detected, it must be released from the envelope or capsid. Viral nucleic acids are released by treating tissue or other samples with a lysis buffer which destroys the protein viral capsid. The nucleic acid is then purified and amplified using PCR, and sequences specific to the virus of interest are detected through single strand nucleic acid probes containing a fluorphore.

Failure to distinguish between free and encapsidated intact viral nucleic acids may generate a false positive result for the presence of the virus in the sample. Preparation of pancrelipase may cause encapsidated viral RNA to be released during the extraction process. The lysis buffer results in the release of the encapsidated RNA into the general environment making it indistinguishable from free RNA. In some cases, the free RNA may constitute short fragments of the original nucleic acid strand.

Because current HEV RNA detection methods do not differentiate between free form RNA or fragments thereof, and encapsidated RNA in pancrelipase, improved detections methods are in need, particularly detection methods that can effectively differentiate between free form and encapsidated RNA, thereby reducing false positive test results.

In a publication by Schielke et al., Virology Journal 2011, 8:487, the investigators evaluated the presence of HEV in a boar liver homogenate. The methodology added ribonuclease (RNase) to the homogenate to degrade all RNA not protected by the viral capsid, prior to RNA amplification. The investigators observed that free RNA was purged from the homogenate by way of the RNase such that subsequent analyses detected only RNA from whole HEV virions (following lysis of the capsid to release the encapsidated RNA). The methods described in this publication are particular to liver homogenate. Persons having ordinary skill in the art would readily understand that enzymes in the pancreas, particularly pancreatic proteases, readily degrade nucleases such that RNase used in a liver extract would not necessarily function in a pancreatic extract.

Accordingly, there exists a need in the art for a method of detection that is able to differentiate between free and encapsidated nucleic acid to avoid the generation of false positive results in biological samples of the pancreas. There also exists a need in the art for a product of a sample that is free from free nucleic acid to detect an intact virus in biological samples of the pancreas.

SUMMARY OF THE INVENTION

Methods for removing substantially all free nucleic acids from pancrelipase comprise treating pancrelipase with an amount of a nuclease and for an amount of time effective to catalyze the degradation of substantially all free nucleic acids, in the pancrelipase. The nuclease is preferably a ribonuclease and more preferably comprises ribonuclease A. The nuclease is preferably a deoxyribonuclease and more preferably ribonuclease and deoxyribonuclease used simultaneously. In some embodiments, the ribonuclease comprises ribonuclease A. The free nucleic acid may comprise DNA or RNA, and preferably comprises viral DNA or RNA, and more preferably comprises viral RNA. The free viral RNA may comprise hepatitis virus RNA. The free hepatitis virus RNA may comprise free Hepatitis E virus RNA. Optionally, the method may comprise treating the pancrelipase with a protease inhibitor in an amount effective to inhibit the protein degradation activity, including ribonuclease degradation activity, of protease enzymes present in the pancrelipase. Pancrelipase devoid of free nucleic acid, including free RNA is provided. Pancrelipase devoid of free RNA, and including free Hepatitis E virus RNA, is provided.

Methods for screening a sample of pancrelipase for Hepatitis E virus contamination comprise treating pancrelipase with an amount of ribonuclease and deoxyribonuclease effective to catalyze the degradation of substantially all free nucleic acids, including free RNA in the pancrelipase, thereby producing pancrelipase substantially devoid of free nucleic acid, including free RNA, inhibiting the RNA degradation activity of the ribonuclease, treating the pancrelipase substantially devoid of free nucleic acid with an agent capable of denaturing the capsid of a Hepatitis E virus in an amount effective to denature the capsid, thereby producing pancrelipase comprising formerly encapsidated Hepatitis E virus RNA, optionally extracting the formerly encapsidated Hepatitis E virus RNA, amplifying the formerly encapsidated Hepatitis E virus RNA, and detecting the amplified formerly encapsidated Hepatitis E virus RNA. The method may further comprise treating the pancrelipase with a protease inhibitor in an amount effective to inhibit the biologic activity of protease enzymes present in the pancrelipase. The ribonuclease may comprise ribonuclease A. The method may be capable of high throughput screening of pancrelipase. Degradation of the free RNA may comprise degrading the RNA to an extent that base sequences associated with the presence of Hepatitis E virus can no longer be detected.

Methods for screening a sample of pancrelipase for Hepatitis E virus contamination comprise treating pancrelipase with a type and concentration of salt capable of precipitating the protein fraction of the pancrelipase in an amount effective to precipitate the protein fraction while leaving the nucleic acids in solution, thereby producing a precipitated pancrelipase protein fraction substantially devoid of free RNA, treating the protein fraction with an agent capable of denaturing the capsid of a Hepatitis E virus in an amount effective to denature the capsid, thereby producing a precipitated pancrelipase protein fraction comprising formerly encapsidated Hepatitis E virus RNA, optionally extracting the formerly encapsidated Hepatitis E virus RNA, amplifying the formerly encapsidated Hepatitis E virus RNA, and detecting the amplified formerly encapsidated Hepatitis E virus RNA. The methods may optionally comprise washing the precipitated protein fraction once or more than once. The methods may optionally comprise washing, re-suspending and re-precipitating the protein fraction, once or more than once. The salt may comprise ammonium sulfate. The method may be capable of high throughput screening of pancrelipase.

A method for producing pancrelipase or a batch of pancrelipase comprises obtaining a pancrelipase extract or batch of pancrelipase extracts, detecting or measuring the amount of free RNA and encapsidated RNA in a sample of the pancrelipase extract, or one or more samples from one or more of the pancrelipase extracts in the batch, validating the pancrelipase extract or the batch of pancrelipase extracts for the presence of free RNA and encapsidated Hepatitis E virus RNA, and incorporating the pancrelipase extract or batch of pancrelipase extract into one or more dosage forms. The method of detecting or measuring RNA comprises treating the pancrelipase or the batch of pancrelipase with an amount of ribonuclease and deoxyribonuclease and for an amount of time effective to catalyze the degradation of substantially all free nucleic acid in the pancrelipase, thereby producing pancrelipase substantially devoid of free nucleic acid, including free RNA, inhibiting the RNA degradation activity of the ribonuclease, treating the pancrelipase substantially devoid of free nucleic acid with an agent capable of denaturing the capsid of a Hepatitis E virus in an amount and for a time effective to denature the capsid, thereby producing pancrelipase comprising formerly encapsidated Hepatitis E virus RNA, amplifying the formerly encapsidated Hepatitis E virus RNA, and detecting the amplified formerly encapsidated Hepatitis E virus RNA.

A solid dosage form of the present invention comprises pancrelipase substantially devoid of free RNA, and one or more pharmaceutically acceptable excipients. The solid dosage form comprises free RNA at least 50% below when compared to free RNA present in a crude pancrelipase extract and can be a powder, a tablet, a mini-tablet, a micro-tablet, an uncoated dosage form, a coated dosage form, a mixture of coated and uncoated dosage forms, a microsphere, a prill, a caplet, a gelcap, a capsule, or a medical food.

A method of treating or preventing a condition or disorder associated with digestive enzyme deficiency in a patient in need thereof, administering an effective amount of the pharmaceutical composition or the dosage form comprising pancrelipase substantially devoid of free RNA. The method of treating or preventing a condition or disorder associated with digestive enzyme deficiency in a patient comprises administering a pharmaceutical composition or dosage form comprising a pancrelipase extract to a patient in need thereof. The method comprises obtaining a pancrelipase extract or batch of pancrelipase extracts, detecting or measuring the amount of free RNA and encapsidated RNA in a sample of the pancrelipase extract, or one or more samples from one or more of the pancrelipase extracts in the batch, validating the pancrelipase extract or the batch of pancrelipase extracts for the presence of free RNA and encapsidated Hepatitis E virus RNA; incorporating the pancrelipase extract or batch of pancrelipase extract into one or more dosage form, and administering an effective amount of the pancreatic enzyme preparation to the patient, wherein the viral infectious load in the pancrelipase extract or the batch of pancrelipase extracts are below a threshold. The patient may be suffering from cystic fibrosis, exocrine pancreatic insufficiency, chronic pancreatitis or any other pancreatic related disease or disease condition

DRAWINGS

DETAILED DESCRIPTION OF THE INVENTION

Figure 1:
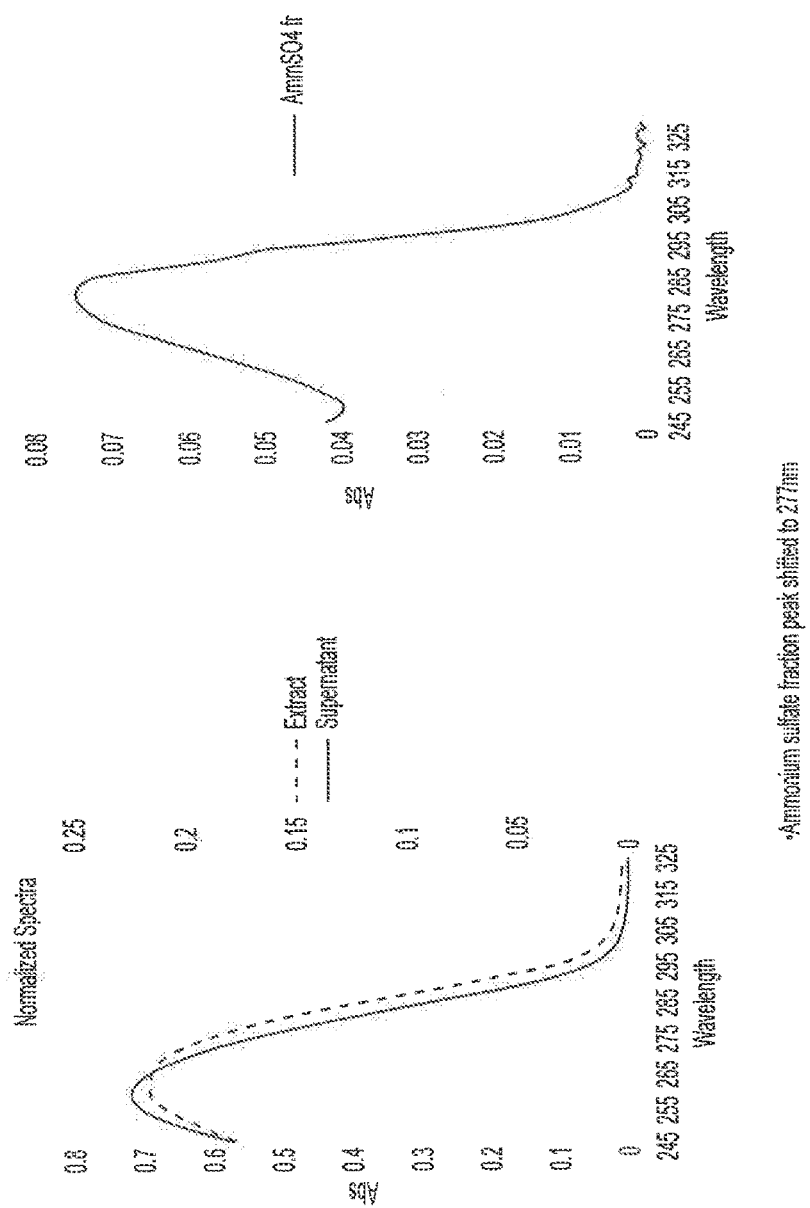
FIG. 1 shows the normalized spectra of ammonium sulfate fractionation of pancrelipase.

Various publications, including patents, published applications, technical articles and scholarly articles are cited throughout the specification. Each cited publication is incorporated by reference herein, in its entirety and for all purposes.

Various terms relating to aspects of the invention are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

The term "patient" refers to a human being or other animal.

Common abbreviations correspond to units of measure, techniques, properties or compounds as follows: "min" means minutes, "h" or "hr" means hour(s), "i" or "μi" means microliter(s), "mL" or "ml" means milliliters), "mM" means millimolar, "M" means molar, and "mmole" means millimole(s).

The term "USP unit" refers to a unit used to measure the potency of a vitamin or drug, that is, the expected biological effects of the vitamin or the drug. For each substance to which this unit applies, the U. S. Food and Drug Administration has determined the biological effect associated with a dose of 1 USP unit. Other quantities of the substance can then be expressed in terms of this standard unit. In most cases, the USP unit is equal to the international unit (IU).

The term "PCR" refers to polymerase chain reaction and the term "RT-PCR" refers to reverse transcriptase polymerase chain reaction.

The term "Amplification" of DNA as used herein denotes the use of polymerase chain reaction (PCR) to increase the concentration of a particular DNA sequence within a mixture of DNA sequences. For a description of PCR, see Saiki et al, Science 1988, 239:487, the disclosure of which is incorporated herein.

The term "therapeutically effective amount" generally refers to the amount of a compound or composition that, when administered to a patient (such as a human) for treating a state, disorder or condition, is sufficient to effect such treatment. The "therapeutically effective amount" will vary depending on the compound or composition, the disease and its severity, and the age, weight, physical condition and responsiveness of the animal to be treated.

The terms "pancrelipase" or "pancrelipase enzymes" or "pancreatin" denote a mixture of several types of enzymes, including amylase, lipase, and protease enzymes, or mixtures thereof having pancreatic origin. Pancrelipase is commercially available, for example from Nordmark Arzneimittel GmbH, Scientific Protein Laboratories LLC, or Sigma Aldrich and similar extracts from porcine, bovine or other mammalian sources may be used.

Pancrelipase comprises a mixture of amylase, lipase, and protease enzymes. Pancrelipase is also known in the art as pancreatin, pancreatic extract or a batch of pancreatic extract. Other active enzymes which may be present in pancrelipase include: (i) active proteases including, but not limited to, trypsin, E.C. (Enzyme Commission Number) without limiting, 3.4.21.4; chymotrypsin, without limiting, E.C. 3.4.21.1; chymotrypsin B, without limiting, E.C. 3.4.21.1; pancreatopeptidase E, without limiting, E.C. 3.4.21.36 and 3.4.21.37; carboxypeptidase A, without limiting, E.C. 3.4.17.1; and carboxypeptidase B, without limiting, E.C. 3.4.17.2; elastase without limiting, E.C. 3.4.21.36; kallikrein without limiting, E.C. 3.4.21.35 (ii) active lipases, including, but not limited to, glycerol ester hydrolase (Lipase), without limiting, E.C. 3.1.1.3; phospholipase A2, without limiting, E.C. 3.1.1.4; and sterol ester hydrolase, without limiting, E.C. 3.1.1.13; (iii) nucleases, such as, but not limited, to ribonuclease, (without limiting, E.C. 2.7.7.16) and deoxyribonuclease, (without limiting, E.C. 3.1.4.5); and (iv) active amylases such as a-Amylase, (without limiting, E.C. 3.2.1.1).

The term "digestive enzyme" as used herein denotes an enzyme in the alimentary tract which breaks down the components of food so that they can be taken or absorbed by the organism. Non-limiting examples of digestive enzymes include pancrelipase (also referred to as pancreatin), lipase, co-lipase, trypsin, chymotrypsin, chymotrypsin B, pancreatopeptidase, carboxypeptidase A, carboxypeptidase B, glycerol ester hydrolase, phospholipase, sterol ester hydrolase, elastase, kininogenase, ribonuclease, deoxyribonuclease, a-amylase, papain, chymopapain, glutenase, bromelain, ficin, β-amylase, cellulase, β-galactosidase, isomaltase, and mixtures thereof. These enzymes may be obtained through extraction from the pancreas or pancreatic juices or produced artificially or obtained from sources other than pancreas such as from microorganisms, bacteria, mold, fungi, plants or other animal tissues, or genetically modified microorganisms, fungi or plants.

The term "lipase" denotes an enzyme that catalyzes the hydrolysis of lipids to glycerol and simple fatty acids. Examples of lipases suitable for the present invention include, but are not limited to, animal lipases (e.g., porcine lipases), bacterial lipases (e.g., *Pseudomonas* lipase and/or *Burkholderia* lipase), fungal lipases, plant lipases, recombinant lipases (e.g., produced via recombinant DNA technology by a suitable host cell, selected from any one of microorganisms, bacteria, yeast, fungi, plants, insects or mammalian host cells in culture, or recombinant lipases which include an amino acid sequence that is homologous or substantially identical to a naturally occurring sequence, lipases encoded by a nucleic acid that is homologous or substantially identical to a naturally occurring lipase-encoding nucleic acid, etc.), synthetic lipase, chemically-modified lipase, and mixtures thereof.

The term "amylase" refers to glycoside hydrolase enzymes that break down starch, for example α-amylases, β-amylases, γ-amylases, acid a-glucosidases, salivary amylases such as ptyalin, etc. Amylases suitable for use in the present invention include, but are not limited to animal amylases, bacterial amylases, fungal amylases (e.g., *Aspergillus* amylase, such as, *Aspergillus oryzae* amylase), plant amylases, recombinant amylases (e.g., produced via recombinant DNA technology by a suitable host cell, selected from any one of microorganisms bacteria, yeast, fungi, plants, insects or mammalian host cells in culture, or recombinant amylases which include an amino acid sequence that is homologous or substantially identical to a naturally occurring sequence, amylases encoded by a nucleic acid that is homologous or substantially identical to a naturally occurring amylase-encoding nucleic acid, etc.), chemically modified amylases, and mixtures thereof.

The term "protease" refers generally to enzymes (e.g., proteinases, peptidases, or proteolytic enzymes) that break peptide bonds between amino acids of proteins. Proteases are generally identified by their catalytic type, e.g., aspartic acid peptidases, cysteine (thiol) peptidases, metallopeptidases, serine peptidases, threonine peptidases, alkaline or semi-alkaline proteases, neutral proteases and peptidases of unknown catalytic mechanism. Non-limiting examples of proteases suitable for use in the present invention include serine proteases, threonine proteases, cysteine proteases, aspartic acid proteases (e.g., plasmepsin) metalloproteases and glutamic acid proteases. In addition, proteases suitable for use in the present invention include, but are not limited to animal proteases, microbial proteases, bacterial proteases, fungal proteases (e.g., an *Aspergillus melleus* protease), plant proteases, recombinant proteases (e.g., produced via recombinant DNA technology by a suitable host cell, selected from any one of bacteria, yeast, fungi, plant, insect or mammalian host cells in culture, or recombinant proteases, which include an amino acid sequence that is homologous or substantially identical to a naturally occurring sequence, proteases encoded by a nucleic acid that is homologous or substantially identical to a naturally occurring protease-encoding nucleic acid, etc.), chemically modified proteases, and mixtures thereof.

Pancrelipase may be derived from animal sources, for example, hog, sheep and bovine. Co-lipase may also be included in pancrelipase. The term "enzyme" includes not only the already activated form, but it also includes the zymogen precursor which is capable of being transformed into the active form in mammalian intestinal fluid. Free RNA comprises polyribonucleotides of any chain length, including fragments thereof, that are not contained, enclosed, or enveloped by cells, viruses, or cellular, organelle, protein, or other structures that ordinarily contain, enclose, or envelope such polyribonucleotides or viral genetic materials. Free RNA comprises cell-free RNA and virus-free RNA, including virus capsid-free RNA. Free RNA may also be referred to as naked RNA. By way of example, but not of limitation, free RNA in a liquid pancrelipase composition comprises polyribonucleotides of cellular or viral origin that are free-floating among the constituents of the pancrelipase. Free RNA are not protected from degradation by the biologic activity of ribonucleases, in contrast to, for example, virus capsid-enclosed RNA which is shielded from ribonucleases through the capsid enclosure. Virus capsid-enclosed RNA may also be referred to as encapsidated RNA or intact virus RNA or intact RNA.

The present invention relates to screening assays for detecting RNA virus contamination of pancreatic extracts. These assays have improved sensitivity over the current state of the art insofar as these assays can differentiate between free viral RNA in the pancreatic extracts (e.g., viral RNA fragments or other RNA resulting from refining and processing the crude pancreatic extract into API or a drug form) and encapsidated viral RNA. The former type of RNA, if amplified and detected in the extract, causes a false positive result of virus contamination, even if the extract does not include any contaminating virus. The latter type of RNA (encapsidated) is representative of a true virus contamination and thus, it is preferred that encapsidated RNA be identified to the exclusion of free RNA.

In some aspects of the present invention, the screening assays include degrading free nucleic acid, with ribonuclease and deoxyribonuclease (RNase and DNase). Any other denaturing agents or chemical inhibitors or chemical agents such as DTT, beta mercaptoethanol may also be used in accordance with the present invention and are considered to be within the scope of the present invention. For example, denaturing agents such as, but not limited to, DTT, enzymes that cleave nucleic acids or exosomes may also be used. Ribonucleases are highly sensitive to pancreatic enzymes, particularly proteases, and other materials present in pancreatic extracts insofar as these enzymes and materials may inhibit the RNA degrading activity of the nuclease, or may even destroy the ribonuclease. It is believed that pancreatic proteases readily catalyze the degradation of ribonucleases, in which case the ribonucleases do not have a chance to degrade RNA in pancreatic extracts. In this respect, it is surprising and unexpected that in the present invention, the ribonucleases successfully degrade free RNA present in the pancreatic extracts.

In some aspects of the present invention, the screening assays comprise methods for screening a pancreatic extract for RNA virus contamination. In preferred embodiments, the methods generally comprise the steps of treating the pancreatic extract with a ribonuclease and deoxyribonuclease, for example, RNase and DNase, in an amount sufficient to effectively catalyze the degradation of substantially all free nucleic acids or fragments thereof, present in the pancreatic extract. Ribonuclease A is a non-limiting example of a ribonuclease the may be used in accordance with the methods. The treating may be carried out for a period of time sufficient to complete the degradation reaction. The treating may be carried out using ribonuclease and deoxyribonuclease simultaneously for a period of time sufficient to complete the degradation reaction. In some embodiments, ribonuclease and deoxyribonuclease may be used consequently or one after the other, in any order and such embodiments are considered to be within the scope of the present invention.

As noted above, RNA or fragments thereof present in the pancreatic extracts and arising from broken capsid of encapsidated intact viruses may give rise to false positive result of viral contamination when extracted together with encapsidated intact viral RNA, which is the true contamination. In order to prevent the false positive results, in preferred embodiments of the invention, ribonuclease and deoxyribonuclease (RNase and DNase) may be added at the beginning of the sample preparation to digest all nucleic acid fragments present in the pancreatic extracts. When the degradation reaction is complete, the pancreatic extract is substantially devoid of free nucleic acids, including free RNA. The free RNA preferably comprises any free virus RNA or fragments thereof present in the pancreatic extract.

Following the completion of the degradation reaction, the methods further comprise inhibiting the RNA degradation activity of the ribonuclease, for example, by treating the pancreatic extract with a ribonuclease inhibitor in an amount effective to inhibit the RNA degradation activity of the ribonuclease or by heating the pancreatic extract to a temperature sufficient to denature the ribonuclease, but not any intact virus capsids present in the extract.

In some embodiments of the present invention, the methods may optionally comprise removal of cellular debris present in the pancreatic extract by precipitating the cellular debris or protein fraction by centrifugation. Centrifugation may be performed at about 1800-15,000 g, for at least about 5 minutes to about 30 minutes, at about 4° C. to about 25° C., following the degradation reaction. Upon precipitation of a pancreatic extract solution, nucleic acids, including free RNA remain in the liquid supernatant, but are not present in the precipitated proteins. The supernatant solution may be further analyzed, while the pellet is further analyzed for the presence of viral RNA precipitated, which may be responsible for false negative results.

In some embodiments of the present invention, the method may optionally comprise filtration of the sample to remove molecules and nucleic acids that are smaller in size, for example, without limiting, lesser than about 1000 kDa. A skilled person would readily know the type and size of filter that may be used. For example, without limiting, filters having 200,000-400,000 MWCO may be used for the filtration. Generally, the solution to be filtered is diluted sufficiently, for example, at about a ratio of 1:25, preferably at a ratio of 1:10, and compared to the starting volume to avoid aggregation of small proteins and polypeptides on the top of the filter. To ensure that the filtered solution is free of small molecules and nucleic acids, the filter may be washed at least once to remove unwanted molecules from the top solution of the filter.

Following the inhibition of the ribonuclease, the methods further comprise denaturing the capsid of any RNA virus present in the pancreatic extract, for example, by treating the extract with an agent capable of denaturing the capsid for a sufficient amount of time necessary to release the encapsidated viral RNA into the pancreatic extract. A denaturing agent may comprise an agent that lyses the virus capsid. Any denaturing or degradation agent may be used in accordance with the present invention. For example, denaturing or degradation agents such as, but not limited to, chemical agents, enzymes, solvents, salts may be used and are considered to be within the scope of the present invention.

The released viral RNA may then be extracted and detected from the pancreatic extract. The extracted RNA, which is the released viral RNA, is then amplified, for example, using an appropriate PCR technique, and the amplified RNA may then be detected. Detection may be quantitative or qualitative, and according to any technique suitable in the art. For example, an evaluation in the linearity of the response in the target concentration and the precision of most representative samples may be used to obtain quantitative measurements. Denaturing of the virus capsid preferably releases the encapsidated RNA into the pancreatic extract, and it is this released, formerly encapsidated RNA that is ultimately detected toward establishing if the pancreatic extract contains a contaminating RNA virus.

In some aspects of the present invention, the screening assays comprise methods for screening a pancreatic extract for RNA virus contamination and detecting the presence of viral contaminants present in the pancreatic extract. In preferred embodiments, the methods comprise screening pancreatic extract for RNA virus contamination and detecting the presence of encapsidated viral RNA contaminants present in the pancreatic extract.

Pancreatic enzymes, including pancreatic proteases present in the extract may inhibit or degrade the ribonuclease enzyme. Accordingly, the methods may comprise inhibiting protease enzymes in the pancreatic extract, for example, by treating the extract with a protease inhibitor in an amount effective to inhibit the biologic activity of protease enzymes present in the extract.

In some aspects, the screening method comprises precipitating the protein fraction of the pancreatic extract with an agent that precipitates the proteins in the extract, but does not co-precipitate nucleic acids. It is believed that viruses, comprising protein capsids, will precipitate along with the other proteins in the extract. Upon precipitation of a pancreatic extract solution, nucleic acids, including free RNA, remain in the liquid supernatant but are not present in the precipitated proteins. The agent may comprise a solvent or salt. A preferred salt is ammonium sulfate. To ensure the precipitate is free of nucleic acids, the precipitate may be washed at least one time.

The nucleic acid-free precipitate may then be reconstituted into a liquid form and subject to further treatment as follows. Following reconstitution of the nucleic acid-free protein fraction of the extract, the methods comprise denaturing the capsid of any RNA virus present in the pancreatic extract, for example, by treating the extract with an agent capable of denaturing the capsid. A denaturing agent may comprise an agent that lyses the virus capsid. Denaturing the capsid is carried out for a time sufficient to denature the capsid and release encapsidated viral RNA into the pancreatic extract. The released viral RNA may be extracted from the reconstituted protein fraction utilizing the known methods in the art. The released viral RNA is then amplified, for example, using an appropriate PCR technique, and the amplified RNA may then be detected. Detection may be quantitative or qualitative, and according to any technique suitable in the art. Denaturing of the virus capsid preferably releases the encapsidated RNA into the reconstituted protein fraction, and it is this released, formerly encapsidated RNA that is ultimately detected to establish if the pancreatic extract contains a contaminating RNA virus.

The pancreatic extract may comprise pancreatic amylase. The pancreatic extract may comprise pancreatic lipase. The pancreatic extract may comprise pancreatic protease enzymes. The pancreatic extract may comprise any combination of amylase, lipase, and protease enzymes. In highly preferred embodiments, the pancreatic extract comprises pancrelipase. In carrying out any of the methods, the pancreatic extract may comprise water, RNase free water or a suitable buffer or a physiologic saline solution.

The methods of the present invention may detect any RNA virus, and preferably RNA viruses that are pathogenic to human beings. Other viruses that could be found in pancrelipase include EMCV (porcine encephalomyocarditis virus, also known as MEV), swine hepatitis virus (including HEV (swine hepatitis E virus)), SVDV (swine vesicular disease virus, also known as PEV9), vesicular exanthema virus, porcine circovirus (including PCV I (porcine circovirus 1)) and PCV2 (porcine circovirus 2)), porcine rotavirus (Rota A), reovirus (including reovirus type 3 which is known as Reo3), foot and mouth disease virus, porcine teschovirus I (PTV 1, also known as PEV 1), porcine adenovirus, and porcine respiratory coronavirus. Enveloped viruses, such as pseudorabies virus, VSV (vesicular stomatitis virus), IFA (influenza A), rabies virus, African swine fever virus, transmissible gastroenteritis virus, classical swine fever virus, West Nile virus, suipoxvirus, hantavirus, porcine cytomegalovirus, porcine lymphotropic herpesvirus, porcine endogenous retrovirus, porcine respiratory reproductive syndrome virus, paramyxovirus, and encephalomyelitis virus could also be found in pancrelipase. See, FDA Antiviral Drugs Advisory Committee Meeting held in December 2008 available on the Worldwide Web at fda.gov/ohrms/dockets/ac/cder08.html#AntiviralDrugs. Pancrelipase could also potentially contain emerging viruses such as emerging enveloped or non-enveloped adventitious agents (e.g., ebola virus) or mutant viruses. Other viruses which can be found in pancrelipase include pseudorabies virus, bovine viral diarrhea virus, picornaviridae (including porcine picornaviridae), reoviridae (including porcine reoviridae), astroviridae (including porcine astroviridae), adenoviridae (including porcine adenoviridae) and hepeviridae (including porcine hepeviridae). In highly preferred embodiments, the RNA virus comprises a hepatitis virus, including Hepatitis A, Hepatitis B, Hepatitis, C, Hepatitis D, and/or Hepatitis E. Hepatitis E is most preferred.

The screening methods may be used for low throughput, or medium throughput screening of pancreatic extracts. The screening methods may also be used for high throughput screening of pancreatic extracts.

Generally, RNA is not quantifiable by spectrometry since the viral RNA preparation has a large amount of carrier RNA and it is difficult to distinguish what portion of the quantified RNA originated from carrier RNA or viral RNA. PCR techniques have been found to be more reliable to quantify RNA against primary and secondary standards.

In accordance with the present invention, a one-step RT-PCR may be incorporated into both, qRT-PCR and nested PCR. The one step RT-PCR reaction may be carried out using degenerate primers targeting the ORF 2 region of encapsidated virus as described in Erker et al. 1999, which is incorporated herein. For example, ORF2 sense may be "GACAGAATTRATTTCGTCGGCTGG" and ORF2 antisense may be "CTTGTTCRTGYTGGTTRTCATAATC". A positive control reaction, containing primary or secondary standard of 2500 IU/ml, and a negative control containing $H_2O$, may be set up simultaneously with the sample reactions. PCR reactions may be carried out using PCR cycling conditions such as, for example, without limiting, 45° C. for 45 minutes, 94° C. for 2 minutes, 40 cycles of 94° C. for 30 seconds, 60° C. for 1 minute, 68° C. for 2 minutes, end of cycle, 7 minutes extension at 68° C. and then a 4° C. hold.

The nested PCR reaction may then be carried out using degenerate primers targeting the amplicon from the PCR reaction. A positive control reaction and a negative control reaction may be set up in tandem using the PCR product obtained from the positive and negative control reactions of the RT-PCR. PCR reactions may be carried out using PCR cycling conditions such as, for example, without limiting, 94° C. for 1 min, 35 cycles of 94° C. for 20 seconds, 55° C. for 30 seconds, 68° C. for 30 seconds, and end of cycle followed by extension and hold cycles. The products obtained from the completed PCR reaction may be electrophoresed on an agarose gel and the samples may be analyzed for base pair size and base pair length.

A quantitative real time PCR analysis may also be performed. A skilled person in the art would readily know the qPCR standardization procedure. Negative and positive controls are included in the PCR and a standard calibration curve is obtained using RNA obtained from viruses at, for example, a concentration ranging from about 500,000 UI/ml to about 25 UI/ml.

Removing free nucleic acid from the pancreatic extract produces a pancreatic extract that is substantially devoid of free nucleic acid, including free RNA. According to the RNA degradation and RNA-excluding protein precipitation described and exemplified herein, the resulting pancreatic extract comprises less free nucleic acid relative to pancreatic extracts prepared according to current methodologies. Removing free RNA from the pancreatic extract produces a pancreatic extract that is substantially devoid of free RNA. According to the RNA degradation and RNA-excluding protein precipitation described and exemplified herein, the resulting pancreatic extract comprises less free RNA relative to pancreatic extracts prepared according to current methodologies. Pancreatic extracts prepared according to the current state of the art contain trace amounts of free RNA, which may be present in the tissue from which the pancreatic extract was obtained, or may be present as an artifact of the processing and refining steps that produce a usable drug form of the pancreatic extract from the crude extract. Such processing and refining steps may lyse or otherwise denature RNA viruses present in the extract, thereby releasing RNA or RNA fragments into the extract, even though the virus source of the RNA is ultimately removed. The pancreatic extract produced according to the methods described herein is more pure than the extracts produced absent these methods or crude pancreatic extract insofar as pancreatic extracts produced according to the present invention are more purified, having less than trace amounts of free RNA, or no free RNA.

In some embodiments of the present invention, the pancreatic extract is substantially devoid of free nucleic acid. In some embodiments, the pancreatic extract is devoid of at least about 100%, 99%, 98%, 95%, 90%, 80%, 70%, or 50% of free RNA present in the pancreatic extract. In preferred embodiments, the pancreatic extract is devoid of about 100% of free RNA present in the pancreatic extract. In other embodiments, the pancreatic extract is devoid of about 99% of free RNA present in the pancreatic extract. In yet other embodiments, the pancreatic extract is devoid of about 98% of free RNA present in the pancreatic extract. In yet other embodiments, the pancreatic extract is devoid of about 90% of free RNA present in the pancreatic extract. In yet other embodiments, the pancreatic extract is devoid of more than about 95% of free RNA present in the pancreatic extract when compared to free RNA present in crude pancreatic extract.

In other embodiments of the present invention, the method of screening comprises detecting at least about 100%, 99%, 98%, 95%, 90%, 80%, 70%, 60%, 50%, 40%, 30%, 20%, 10%, 8%, 5%, 4%, 3%, 2%, or 1% encapsidated viral RNA present in the pancreatic extract. In preferred embodiments, the method of screening comprises detecting about 100% encapsidated viral RNA present in the pancreatic extract. In other embodiments, the method of screening comprises detecting about 98% encapsidated viral RNA present in the pancreatic extract. In other embodiments, the method of screening comprises detecting about 95% encapsidated viral RNA present in the pancreatic extract. In other embodiments, the method of screening comprises detecting about 90% encapsidated viral RNA present in the pancreatic extract. In other embodiments, the method of screening comprises detecting about 5% encapsidated viral RNA present in the pancreatic extract. In other embodiments, the method of screening comprises detecting about 2% encapsidated viral RNA present in the pancreatic extract.

In some aspects of the present invention, the method of screening comprises detecting about 50,000 IU/ml to about 10,000 IU/ml encapsidated viral RNA present in the pancreatic extract. In one embodiments, pancrelipase comprising one or more pancreatic enzymes having reduced viral infectivity after removal of viral contaminants, including encapsidated viral RNA can have a viral infectivity of at least about 1 log below, of at least about 2 logs below, or at least about 3 logs below that of a pancrelipase extract not treated using the methods described herein and as measured by standardization curve of qPCR described and exemplified herein.

Pancreatic extracts substantially devoid of free RNA are featured in accordance with the invention. The present invention as described and exemplified herein detects about 100% free RNA. Such pancreatic extracts may comprise pancreatic amylase. Such pancreatic extracts may comprise pancreatic lipase. Such pancreatic extracts may comprise pancreatic protease enzymes. Such pancreatic extracts may comprise any combination of amylase, lipase, and protease enzymes. In highly preferred aspects, such pancreatic extracts comprises pancrelipase.

The present invention features methods for removing substantially all free nucleic acid, including free RNA from a pancreatic extract and detecting encapsidated viral RNA. In general, the methods comprise treating the pancreatic extract with an amount of ribonuclease and deoxyribonuclease effective to catalyze the degradation of substantially all free nucleic acid, including free RNA, in the extract and detecting encapsidated viral RNA present in the pancreatic extract. The ribonuclease may comprise ribonuclease A. The free RNA may comprise free viral RNA. The free RNA may comprise free hepatitis virus RNA. In preferred embodiments, the free RNA comprises free Hepatitis E virus RNA. Pancreatic extracts produced according to such methods are also provided. Pancrelipase produced according to such methods is also provided.

In one aspect of the present invention, pancrelipase produced in accordance with the present invention may be incorporated or formed into a pharmaceutical composition, e.g., in admixture with a suitable pharmaceutical excipient, diluent and/or carrier selected with regard to the intended route of administration and standard pharmaceutical practice. In one embodiment of the present invention, compositions and dosages forms comprise at least one digestive enzyme. In one embodiment, the compositions of the invention can be formulated for administration in any convenient way for use in a human. Pancrelipase can be administered as an oral dosage form. Oral dosage forms include powders, tablets, mini-tablets, micro-tablets, uncoated dosage forms, coated dosage forms, microspheres, prills, caplets, gelcaps, capsules, and medical foods. Tablets, for example, can be made by compression techniques known in the art. Typically, pancrelipase is orally administered in the form of enteric-coated mini-microspheres to avoid acid-mediated lipase inactivation and to ensure gastric emptying of enzymes. In some embodiments, pancrelipase may be orally administered in the form of enteric-coated and uncoated mini-microspheres. In some other embodiments, pancrelipase may be orally administered in parallel or along with nutrients.

Suitable pharmaceutically acceptable excipients include, but are not limited to, diluents, binding agents, lubricants, glidants, disintegrants, and coloring agents. Other components such as preservatives, stabilizers, dyes and flavoring agents may be included in the dosage form. Examples of preservatives include sodium benzoate, ascorbic acid and esters of p-hydroxybenzoic acid. Antioxidants and suspending agents may be also included. Pharmaceutically acceptable excipients, diluents, and carriers for therapeutic use are known in the pharmaceutical art, and are described, for example, in Remington: The Science and Practice of Pharmacy, Lippincott Williams & Wilkins (A. R. Gennaro edit. 2005).

A dosage form or batch of dosage forms, where each dosage form comprises pancrelipase can be evaluated or validated by the method described herein. In one embodiment of the present invention, a batch of dosage forms, the batch can be evaluated or validated by detecting or measuring the amount of infectious virus or viral RNA or fragments thereof present in one or more dosage forms selected from the batch. In yet additional aspects, the invention relates to a method for producing pancrelipase by any of the aforementioned detection and screening methods.

Yet another aspect of the present invention is a method for producing pancrelipase or a batch of pancrelipase by (a) obtaining a pancrelipase extract or batch of pancrelipase extracts, and (b) (i) detecting or measuring the amount of free RNA and encapsidated RNA in a sample of the pancrelipase extract, or one or more samples from one or more of the pancrelipase extract in the batch, by the aforementioned detection method, or (ii) validating the pancrelipase extract or the batch of pancrelipase extracts by the aforementioned screening and detecting method. The method can further include the step of (iii) incorporating the pancrelipase extract or batch of pancrelipase extract into one or more dosage forms.

In one aspect, the pancrelipase extract or batch of pancrelipase extracts are validated if the measured viral content is below a threshold level. In the event the pancrelipase extract or batch of pancrelipase extracts have a viral content above the threshold level, the pancrelipase extract or pancrelipase extracts can be further processed to reduce their viral content and again subject to the validation process.

Yet another aspect of the present invention is a method of producing a dosage form or a batch of dosage forms by (a) obtaining a dosage form or batch of dosage forms, each dosage form containing a pancrelipase extract, and (b) (i) detecting or measuring the amount of infectious virus, comprising encapsidated RNA in the dosage form, or in one or more of the dosage forms in the batch by the aforementioned detection method, or (ii) validating the dosage form or batch of dosage forms by the aforementioned validation method.

One aspect of the present invention provides a method of treating or preventing a condition or disorder associated with digestive enzyme deficiency in a patient, comprising administering the pharmaceutical composition or dosage form comprising a pancrelipase extract produced by the methods of the present invention to a patient (e.g., a mammal such as a human) in need thereof. In one embodiment, the invention provides a method of treating or preventing a disorder or condition associated with digestive enzyme deficiency, comprising administering the composition or dosage form comprising a pancrelipase extract produced by the methods of the present invention to a patient in need thereof, wherein the composition or dosage form comprises, in addition to the digestive enzymes, at least one proton pump inhibitor, or one antacid, or other medicament which increases gastrointestinal (GI) pH. In one embodiment, the present invention provides a method of treating or preventing a disorder or condition associated with digestive enzyme deficiency, comprising administering a composition or dosage form comprising a pancrelipase extract produced by the methods of the present invention, in combination with a dosage form comprising at least one proton pump inhibitor, one antacid, or other medicament which increases GI pH.

Disorders or conditions that can be treated with the composition or dosage forms comprising a pancrelipase extract produced by the methods of the present invention include conditions in which the patient has no or low levels of digestive enzymes or in which patients require digestive enzyme supplementation. For example, such conditions can include exocrine pancreatic insufficiency, cystic fibrosis, chronic pancreatitis, other pancreatic diseases (e.g., hereditary, post-traumatic and allograft pancreatitis, hemochromatosis, Shwachman syndrome, lipomatosis, or hyperparathyroidism), side-effects of cancer or cancer treatment, side effects of surgery (e.g., gastrointestinal bypass surgery, Whipple procedure, total pancreatectomy, etc.) or other conditions in which pancreatic enzymes cannot reach the intestine, poor mixing (e.g., Billroth II gastrectomy, other types of gastric bypass surgery, gastrinoma, etc.), side effects of drug treatments such as treatment with metformin or those drugs used to treat the symptoms of HIV and autoimmune diseases such as diabetes in which the pancreas may be compromised, obstruction (e.g., pancreatic and biliary duct lithiasis, pancreatic and duodenal neoplasms, ductal stenosis), malabsorption associated with celiac disease, food allergies and aging.

Yet another aspect of the present invention is a method of controlling or treating a patient with partial or complete exocrine pancreatic insufficiency by administering to patient in need thereof, the pancrelipase extract produced by the methods of the present invention. The method may further comprise (i) obtaining a pancreatic enzyme preparation, (ii) detecting or measuring the amount of infectious virus in the pancreatic enzyme preparation by the aforementioned detection or screening method, and (iii) administering an effective amount of the pancreatic enzyme preparation to the patient when the infectious load in the pancreatic enzyme preparation is below a threshold level. The pancreatic insufficiency can be caused by cystic fibrosis (CF), chronic pancreatitis due to alcohol use or other causes, surgery (pancreaticoduodenectomy or Whipple's procedure, with or without Wirsung duct injection, total pancreatectomy), obstruction (pancreatic and biliary duct lithiasis, pancreatic and duodenal neoplasms, ductal stenosis), other pancreatic disease (e.g., hereditary, post traumatic and allograft pancreatitis, hemochromatosis, Shwachman's Syndrome, lipomatosis, and hyperparathyroidism), and poor mixing (Billroth II gastrectomy, other types of gastric bypass surgery, gastrinoma).

The following examples are provided to describe the present invention in greater detail. They are intended to illustrate, not to limit, the present invention.

EXPERIMENTS

Example 1

Detection of HEV Contamination in Pancrelipase Through RNase Removal of Free Viral RNA and Quantification of Encapsidated Viral RNA by qPCR A series of experiments will evaluate the removal of free viral RNA from pancrelipase via treatment with RNase A. These experiments will also evaluate the effects of protease inhibitors, RNase inhibitors, and virus denaturing buffer on RNase A treatments. It is believed that heterologous RNase A will catalyze the destruction of free viral RNA in the pancrelipase, despite the co-presence of pancreatic proteases and other pancreatic enzymes that are known to inactivate RNase A.

Pancrelipase will be prepared as a 10% (w/v) solution in either RNase-free water or denaturing buffer, such as guanidium thiocyanate or proteinase K. Certain experimental groups will then be treated with 7000 units/ml of RNase A, and certain sub-groups will be further treated with either a protease inhibitor or an RNase inhibitor. Each experimental group will be incubated at 37 degrees C. for one hour, followed by an evaluation of protease activity or RNase activity using commercially available quantitative protease assay kits and quantitative RNase assay kits.

Following enzyme activity testing, each experimental group will be spiked with either naked (not encapsidated) HEV (WHO standard) or intact (encapsidated) HEV (WHO standard), and incubated at about 37 degrees C. for about one hour. Table 1. Incubation conditions will be fine-tuned to minimize protease activity and maximize RNase activity and are presented in Table 1 below.

TABLE 1

| (Experimental Group): medium | RNase A treatment | Inhibitor | HEV spike |
|---|---|---|---|
| (A): 10% Pancrelipase in denaturing buffer | Yes | N/A | Naked |
| (B): 10% Pancrelipase in denaturing buffer | Yes | N/A | Intact |
| (C): 10% Pancrelipase in water | No | N/A | Naked |
| (D): 10% Pancrelipase in water | No | N/A | Intact |
| (E): 10% Pancrelipase in water | Yes | Protease | Naked |
| (F): 10% Pancrelipase in water | Yes | Protease | Intact |
| (G): 10% Pancrelipase in water | Yes | RNase | Naked |
| (H): 10% Pancrelipase in water | Yes | RNase | Intact |

After incubation with HEV, each sample will be subject to denaturing of the virus using a virus assay kit. Subsequently, samples will be evaluated for residual RNase activity (quantitative RNase assay kits), followed by extraction of RNA from each sample. The extracted samples will be treated with an RNase inhibitor, and incubated in the presence of the inhibitor for about 30 minutes followed by further assessment of residual RNase activity (quantitative RNase assay kits). All samples will then be amplified, with RNA amounts quantitated by qPCR. Expected results are presented in Table 2 below.

In parallel to the experimental groups, three positive control samples will be assessed according to the basic protocol outlined above. Two positive controls will receive RNase treatment, and one positive control will not receive RNase treatment. All three controls will be treated with a protease inhibitor. One positive control will be spiked with both naked and intact HEV (WHO standard)(control 1), one positive control will be spiked with naked HEV only (control 2), and one positive control will be spiked with intact HEV only (control 3). Expected results are presented in Table 2 below.

TABLE 2

| Experimental Group or Control Group | Recovery | Assessment |
|---|---|---|
| A | RNA recovered | Demonstrate suitability of denaturing treatment on RNase. |
| B | Intact HEV recovered | Demonstrate suitability of denaturing treatment on protease. |
| C | RNA not recovered | Demonstrate action of pancreatic nucleases on naked HEV. |
| D | Intact HEV recovered | Assessment of the ability of pancreatic proteases to digest viral capsid; Digestion of RNA might occur. |

TABLE 2-continued

| Experimental Group or Control Group | Recovery | Assessment |
|---|---|---|
| E | RNA not recovered | RNase not expected to be inactivated by protease inhibitor; RNA of naked HEV should be digested. |
| F | Intact HEV recovered | Demonstrate protease inhibitor prevents digestion of virus capsid; RNase should be ineffective on RNA in intact virus. |
| G | RNA not recovered | Demonstrate RNase inhibitor prevents digestion of naked RNA. |
| H | Intact HEV recovered | Assess the ability of pancreatic proteases to digest viral capsid; Naked RNA should be completely digested. |
| Control 1 | RNA and intact HEV recovered | Assess protease inhibitor effect (or lack thereof) on PCT amplification. |
| Control 2 | RNA not recovered | Demonstrate protease inhibitors do not inactivate RNase A. |
| Control 3 | Intact HEV recovered | Demonstrate protease inhibitors do not inactivate RNase A; But, RNase should be ineffective at digesting encapsidated viral RNA. |

Example 2

Detection of HEV Contamination in Pancrelipase Through Precipitation of the Protein Fraction and Quantification of Encapsidated Viral RNA by qPCR As an alternative approach to RNase treatment, the protein fraction of pancrelipase may be precipitated from solution using a solvent or a salt in a way that the nucleic acids, including free RNA, remain in solution and do not remain in the protein precipitate. In preliminary experiments, it was observed that ammonium sulfate can be used to precipitate the protein fraction of pancrelipase with free nucleic acids from the pancrelipase remaining in the liquid fraction. The preliminary experiment is set forth in FIG. 1. In FIG. 1, the dominant peak in the dissolved pancrelipase is at 260 nm, a wavelength associated with nucleic acids, and the resuspended precipitated protein fraction (less the discarded supernatant) shows a peak at 277 nm, a wavelength associated with protein in solution.

With intact viruses in the reconstituted precipitated fraction, this fraction will be treated with agents to denature the virus capsid, thereby releasing viral RNA into the solution. The released viral RNA will then be amplified, and the amplified RNA will be detected with HEV RNA sequence-specific probes.

Example 3

Quantification of HEV Encapsidated Viral RNA for Spiking

A series of experiments will evaluate quantitative characterization of HEV encapsidated infected human serum. These experiments will also evaluate the amount of viral RNA for spiking and calibration purposes as shown in Example 4. These experiments generally use the Ceeram Live technology HEV qPCR kit (http://www.ceeram-tools.com/kit-hepatitis-e-virus-kit.html) that is commercially available for qPCR determination (referred to as Ceeram kit). One skilled in the art would readily know how to use the Ceeram kit. Although the Ceeram kit is used in the following experiments, the method of quantification is not limited to the Ceeram kit. Any other technology that may be available to the skilled person in the art to quantify the viral RNA is considered to be within the scope of the subject matter of the present invention.

Human serum is diluted to 250,000 IU/ml solution. Six separate experiments (experiments 1-6) are carried out by adding 80 µl of diluted human serum to 700 µl of DNase and RNase solution resulting in 25,641 IU/ml human serum solution. It is critical to digest all free RNA and extract the encapsidated viral RNA from intact viruses to achieve accurate amount of intact virus RNA for spiking pancrelipase samples. Amount of RNase and DNase necessary for degradation of free RNA may be used. For example, about 0.5 U/ml of RNase and 50 µg/ml DNase may be used to digest free RNA. The solution is vortexed for about 30 seconds and the viral RNA, after nucleases inhibition and RNA extraction, is quantified using the Ceeram kit. Quantification of viral RNA is evaluated against the WHO HEV standard 6329/10, which is incorporated herein and is available at: http://whqlibdoc.who.int/hq/2011/WHO_BS_2011.2175_eng.pdf.

The amount of intact virus RNA will be taken into account for spiking pancreatin samples in order to detect the presence of encapsidated viral RNA in the pancreatic extract. Tables 3a and 3b set forth the standard curves generated using the WHO standard for quantification of intact HEV virus in human serum sample and is presented below. Quantification of intact HEV virus in human serum is set forth and is presented in Table 4 below.

TABLE 3a

Calibration curve for experiments 1-3.

| Standard Concentration (IU/ml) | Ct | Mean Ct |
|---|---|---|
| 250,000 | 27.917 | 27.845 |
|  | 27.666 |  |
|  | 27.952 |  |
| 25,000 | 30.610 | 30.678 |
|  | 30.583 |  |
|  | 30.840 |  |
| 2500 | 33.298 | 33.510 |
|  | 33.520 |  |
|  | 33.712 |  |
| 250 | 36.428 | 36.335 |
|  | 37.615 |  |
|  | 34.961 |  |
| 25 | 39.174 | 38.869 |
|  | 39.058 |  |
|  | 38.374 |  |
| Slope | −2.83 |  |
| $R^2$ | 0.99 |  |
| Efficiency | 125.6% |  |

TABLE 3b

Calibration curve for experiments 4-6.

| Standard Concentration (IU/ml) | Ct | Mean Ct |
|---|---|---|
| 250,000 | 28.889 | 28.932 |
|  | 28.940 |  |
|  | 28.968 |  |
| 25,000 | 32.299 | 32.107 |
|  | 32.001 |  |
|  | 32.022 |  |

TABLE 3b-continued

Calibration curve for experiments 4-6.

| Standard Concentration (IU/ml) | Ct | Mean Ct |
|---|---|---|
| 2500 | 34.357 | 34.451 |
|  | 34.359 |  |
|  | 34.638 |  |
| 250 | 36.770 | 37.423 |
|  | Undetermined |  |
|  | 38.076 |  |
| 25 | 38.119 | 37.972 |
|  | 37.826 |  |
|  | Undetermined |  |
| Slope | −2.78 |  |
| $R^2$ | 0.99 |  |
| Efficiency | 128.8% |  |

TABLE 4

| Sample | Replicate | Ct | IU per reaction | IU per ml | Mean Ct | Mean IU per ml | Expected (IU/ml) | Recovery % | St Dev | CV % |
|---|---|---|---|---|---|---|---|---|---|---|
| 1 | 1 | 29.562 | 449.09 | 14,370.77 | 29.54 | 14,652.2 | 25,641 | 57.14 | 720.8 | 4.9 |
|  | 2 | 29.584 | 441.08 | 14,114.52 |  |  |  |  |  |  |
|  | 3 | 29.472 | 483.48 | 15,471.30 |  |  |  |  |  |  |
| 2 | 1 | 29.519 | 465.51 | 14,896.16 | 29.49 | 15,239.9 | 25,641 | 59.44 | 988.4 | 6.5 |
|  | 2 | 29.554 | 452.17 | 14,469.35 |  |  |  |  |  |  |
|  | 3 | 29.404 | 511.07 | 16,354.31 |  |  |  |  |  |  |
| 3 | 1 | 28.915 | 760.58 | 24,338.54 | 28.85 | 25,590.3 | 25,641 | 99.80 | 1,136.8 | 4.4 |
|  | 2 | 28.840 | 808.57 | 25,874.18 |  |  |  |  |  |  |
|  | 3 | 28.808 | 829.95 | 26,558.29 |  |  |  |  |  |  |
| 4 | 1 | 30.207 | 537.86 | 17,211.41 | 30.48 | 13,531.5 | 25,641 | 52.77 | 3,754.9 | 27.7 |
|  | 2 | 30.798 | 303.31 | 9,705.82 |  |  |  |  |  |  |
|  | 3 | 30.444 | 427.42 | 13,677.40 |  |  |  |  |  |  |
| 5 | 1 | 30.553 | 384.62 | 12,307.74 | 30.43 | 13,878.5 | 25,641 | 54.13 | 1,449.7 | 10.4 |
|  | 2 | 30.338 | 473.91 | 15,165.14 |  |  |  |  |  |  |
|  | 3 | 30.408 | 442.58 | 14,162.60 |  |  |  |  |  |  |
| 6 | 1 | 30.460 | 420.91 | 13,469.23 | 30.36 | 15,348.8 | 25,641 | 59.86 | 5,118.3 | 33.3 |
|  | 2 | 29.990 | 660.66 | 21,141.16 |  |  |  |  |  |  |
|  | 3 | 30.629 | 357.37 | 11,435.96 |  |  |  |  |  |  |
| Overall Mean (samples 1-6) |  |  |  |  |  | 16,373.5 |  | 63.86 | 17.8 | 27.9 |

The results indicate that HEV intact virus recovery of 63.86% was obtained with HEV intact virus concentration of about 16,375.5 IU/ml. Additional studies were performed to evaluate the critical parameters that may affect the recovery of intact HEV virus in digestion procedure such as sample extraction, pH interference, incubation step interference, DTT interference.

Quantification of HEV Free RNA for Spiking

A series of six RNA isolations is carried out using 160 μl aliquots of HEV infected human serum diluted to 250,000 IU/ml solution of HEV infected human serum. Each aliquot is equivalent to about 40,000 IU/ml solution of human serum. RNA extraction is performed to obtain free HEV RNA, using RNA extraction kit. One skilled in the art would readily know how to extract RNA using a commercially available RNA extraction kit. An aliquot of final elution volume obtained from the RNA extraction is assayed against the HEV WHO standard curve. The amount of quantified free RNA is used to calculate the accurate amount of free RNA spiked on pancrelipase solution. The standard curve generated using the WHO standard for quantification of extracted free RNA in human serum sample is presented in Table 5 below. Quantification of free HEV RNA prepared for the spiking experiments is presented in Table 6 below.

TABLE 5

| Standard Concentration (IU/ml) | Ct | Mean Ct |
|---|---|---|
| 250,000 | 28.889 | 28.932 |
|  | 28.940 |  |
|  | 28.968 |  |
| 25,000 | 32.299 | 32.107 |
|  | 32.001 |  |
|  | 32.022 |  |
| 2500 | 34.357 | 34.451 |
|  | 34.359 |  |
|  | 34.638 |  |
| 250 | 36.770 | 37.423 |
|  | Undetermined |  |
|  | 38.076 |  |
| 25 | 38.119 | 37.972 |
|  | 37.826 |  |
|  | Undetermined |  |
| Slope | −2.78 |  |
| $R^2$ | 0.99 |  |
| Efficiency | 128.8% |  |

TABLE 6

| Extraction | Replicate | Ct | IU per reaction | IU per ml | Ct Mean | Mean IU per ml | St Dev | CV % |
|---|---|---|---|---|---|---|---|---|
| 1 | 1 | 27.527 | 2737.826 | 273782.6 | 27.470 | 287120.2 | 13345.64 | 4.6 |
|  | 2 | 27.413 | 3004.579 | 300457.9 |  |  |  |  |
| 2 | 1 | 27.472 | 2863.210 | 286321.1 | 27.373 | 311349.7 | 35170.96 | 11.3 |
|  | 2 | 27.274 | 3363.784 | 336378.4 |  |  |  |  |

TABLE 6-continued

| Extraction | Replicate | Ct | IU per reaction | IU per ml | Ct Mean | Mean IU per ml | St Dev | CV % |
|---|---|---|---|---|---|---|---|---|
| 3 | 1 | 27.550 | 2685.515 | 268551.5 | 27.450 | 292485.8 | 45952.25 | 15.7 |
|   | 2 | 27.349 | 3164.201 | 316420.1 |   |   |   |   |
| 4 | 1 | 27.771 | 2245.426 | 224542.6 | 27.649 | 249122.9 | 27823.45 | 11.2 |
|   | 2 | 27.528 | 2737.031 | 273703.1 |   |   |   |   |
| 5 | 1 | 27.537 | 2717.031 | 271703.1 | 27.492 | 281791.6 | 15121.68 | 5.4 |
|   | 2 | 27.448 | 2918.802 | 291880.2 |   |   |   |   |
| 6 | 1 | 27.580 | 2622.811 | 262281.1 | 27.599 | 258199.8 | 5771.90- | 2.2 |
|   | 2 | 27.619 | 2541.184 | 254118.4 |   |   |   |   |
| Pool | 1 | 27.330 | 3214.991 | 321499.1 | 27.352 | 316167 | 22338.31 | 7.1 |
|   | 2 | 24.450 | 2916.452 | 291645.2 |   |   |   |   |
|   | 3 | 27.278 | 3353.570 | 335356.8 |   |   |   |   |

The mean concentration from the pooled samples is used as the standard concentration to prepare the dilutions for the spiking of free HEV RNA in controlled digestion experiments as described below in Example 4. The concentration of the free HEV RNA from the pooled samples is about 316167 IU/ml having CV of 7.1%.

Example 4

Controlled Digestion of Spiked Pancrelipase Samples

Experiments were performed in duplicate on samples containing pancrelipase spiked with free or intact HEV (treated pancreatin) with and without centrifugation step. Treated positive control samples (no pancrelipase) spiked with free or intact HEV are prepared using the same protocol.

Treated positive control 1 is spiked with naked (free) HEV RNA and Treated positive control 2 is spiked with intact (encapsidated) HEV. Treated positive control 1 (RNase-free water spiked with free HEV RNA) is prepared by adding 0.4 ml of RNase free water containing 50 µg DNase/ml and 0.5 U RNase/ml to 46 µl of 250,000 IU/ml naked RNA, which is equivalent to 316,167 IU/ml as described in Example 3 and exemplified herein. These result in a solution having a nominal concentration of 25,785 IU/ml free HEV RNA in 0.446 ml spiked suspension. The solution is allowed to be digested by the RNase and DNase for about 1 hour at room temperature and 9 µl DTT (1,4-dithiothreitol) at a concentration of 1M is added to the solution to inhibit the RNase and DNase activity. The solution is further incubated for about 1 hour at 37° C. The nominal concentration of the spiked naked HEV RNA in the final sample volume of 0.455 ml is about 25,275 IU/ml. Samples aliquots with and without the centrifugation step is extracted and further analyzed, after being stored overnight at −80° C. Following RNase and DNase inhibition, RNA extraction is performed and RNA is extracted and quantified by qPCR.

Treated positive control 2 (RNase-free water spiked with encapsidated HEV RNA) is spiked with intact (encapsidated) HEV RNA and is prepared by adding 0.4 ml of RNase free water containing 50 µg DNase/ml and 0.5 U RNase/ml to 46 µl of 250,000 IU/ml Hepatitis E virus infected human serum, which is equivalent to 250,000 IU/ml as described in Example 3 and exemplified herein. These result in an intact (encapsidated) HEV RNA solution of 25,785 IU/ml in the 0.446 ml spiked suspension. The solution is allowed to be digested by the RNase and DNase for about 1 hour at room temperature and 9 µl DTT at a concentration of 1M is added to the solution to inhibit RNase and DNase degradation reaction. The solution is further incubated for 1 hour at 37° C. The nominal concentration of the spiked naked HEV RNA in the final sample volume of 0.455 ml is about 25,275 IU/ml. Sample aliquots with and without centrifugation step is extracted and further analyzed, after being stored overnight at −80° C. Following RNase and DNase inhibition, RNA extraction is performed and RNA is extracted and quantified by qPCR.

Treated pancreatin 1 (pancrelipase suspension spiked with free HEV RNA) having a concentration of 0.1 g pancrelipase/ml, sample volume of 0.4 ml containing 50 µg DNase/ml and 0.5 U RNase/ml is spiked with 46 µl of 250,000 IU/ml Hepatitis E naked RNA to obtain a solution of 25,785 IU/ml in the 0.446 ml spiked pancrelipase suspension. The solution is allowed to be digested by the RNase and DNase for about 1 hour at room temperature and 9 DTT at a concentration of 1M is added to the solution to inhibit RNase and DNase degradation reaction. The solution is incubated for 1 hour at 37° C. The nominal concentration of the spiked naked HEV RNA in the final sample volume of 0.455 ml is about 25,275 IU/ml. Sample aliquots with and without centrifugation step is extracted and further analyzed after being stored overnight at −80° C. Following RNase and DNase inhibition, RNA extraction is performed and RNA is extracted and quantified by qPCR.

Treated pancreatin 2 (pancrelipase suspension spiked with encapsidated HEV RNA) at a concentration of 0.1 g pancrelipase/ml, sample volume of 0.4 ml containing 50 µg DNase/ml and 0.5 U RNase/ml is spiked with 46 µl of 250,000 IU/ml Hepatitis E intact virus infected human serum to obtain a solution of 25,785 IU/ml in the 0.446 ml spiked pancrelipase suspension. The solution is allowed to be digested by the RNase and DNase for about 1 hour at room temperature and 9 µl DTT at a concentration of 1M is added to the solution to inhibit RNase and DNase degradation reaction. The solution is incubated for 1 hour at 37° C. The nominal concentration of the spiked intact HEV RNA in the final sample volume of 0.455 ml is about 25,275 IU/ml. Sample aliquots with and without centrifugation step is extracted and further analyzed after being stored overnight at −80° C. Following RNase and DNase inhibition, RNA extraction is performed and RNA is extracted and quantified by qPCR. The experiment is repeated on day 2 and the results are analyzed.

Figure 2:
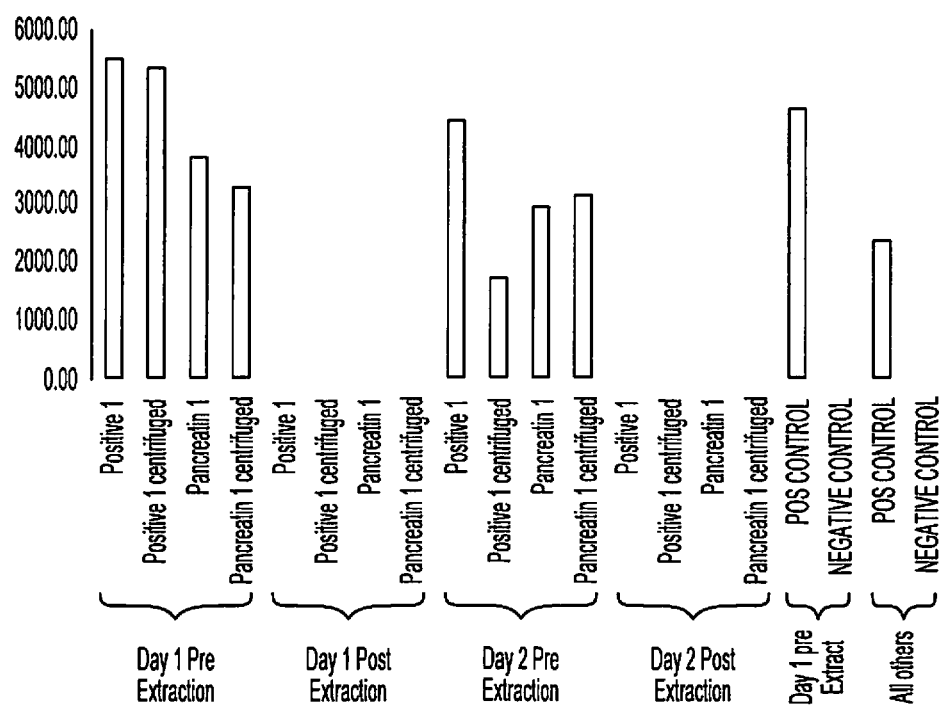
FIG. 2 shows the histogram plot of corrected values for an RNase Alert assay of the present invention.

FIG. 2 shows the histogram plot for the corrected values of RNase alert assay. RNase alert assay is carried out to determine complete deactivation in the nucleases inhibition step before lysis of the viral capsid and the extraction/qPCR analysis of the formerly encapsidated RNA. One skilled in the art would readily know how to perform RNase alert assay, which is commercially available at https://www.lifetechnologies.com/order/catalog/product/AM1964.
WHO standard curve for calibration for the experiments performed on day 1 and day 2 are presented in Tables 7 and 8, respectively.

TABLE 7

WHO Standard curve
Day 1

| Standard concentration (IU/ml) | Ct | Mean Ct | IPC Ct |
|---|---|---|---|
| 250,000 | 28.306 | 28.42 | 27.840 |
|  | 28.527 |  | 27.901 |
| 25,000 | 32.104 | 32.02 | 28.159 |
|  | 31.944 |  | 28.790 |
| 2,500 | 36.901 | 36.89 | 28.025 |
|  | 36.880 |  | 28.049 |
| 250 | 39.093 | 39.21 | 27.955 |
|  | 39.317 |  | 28.048 |
| 25 | No Ct | No Ct | 28.358 |
|  | No Ct |  | 28.224 |
| Slope | −3.671 |  |  |
| $R^2$ | 0.989 |  |  |
| Efficiency | 87.242% |  |  |

TABLE 8

WHO Standard curve
Day 2

| Standard concentration (IU/ml) | Ct | Mean Ct | IPC Ct |
|---|---|---|---|
| 250,000 | 28.494 | 28.49 | 28.025 |
|  | 28.482 |  | 28.192 |
| 25,000 | 31.943 | 31.92 | 28.264 |
|  | 31.899 |  | 28.122 |
| 2,500 | Failed | — | 28.006 |
|  | Failed |  | 28.324 |
| 250 | 38.438 | 38.17 | 28.235 |
|  | 37.893 |  | 28.005 |
| 25 | No Ct | No Ct | 27.970 |
|  | No Ct |  | 28.051 |
| Slope | −3.209 |  |  |
| $R^2$ | 0.998 |  |  |
| Efficiency | 104.939% |  |  |

Standard curves are generated for day 1 and day 2. An $R^2$ value of 0.989 and efficiency of 87.24% was obtained on day 1 and $R^2$ value of 0.998 and efficiency 104.9% was obtained on day 2.

Both standard curves for day 1 and day 2 are considered to be adequate for evaluation of the data. Treated positive control 1 spiked with naked (free) HEV RNA showed no Ct reading indicating that no HEV nucleic acid is present in the sample after the digestion/degradation reaction. This confirmed that the experimental control will remove any residual naked (free) RNA nucleic acid, which is not carried over after the extraction process.

Treated positive control 2 spiked with intact HEV provided a recovery of greater than 100% against the nominal spiked concentration based on 250,000 IU/ml stock solution used for spiking. The recovery value against the actual spiked concentration (with potency of 432,488 IU/ml of the stock solution used for spiking) is around 100% for three of the four tested samples. Quantification of free and intact HEV RNA in Treated Positive samples is presented in Table 9.

Treated pancreatin 1 (pancrelipase suspension spiked with naked RNA) demonstrated complete digestion of the input material on both day 1 and day 2 of the experiment. This is confirmed by the lack of Ct reading in the assay. In comparison to Treated positive control 2, recovery of intact HEV in Treated pancreatin 2 is lower in presence of pancrelipase, either with or without centrifugation. Higher concentration of intact HEV is observed in absence of centrifugation, due to the presence of additional components in the pancrelipase that may lead to the degradation of intact virus and viral recovery is reduced possibly due to aggregation of the virus in the suspension.

Results obtained on day 1 and day 2 of the controlled digestion on treated pancreatin (pancrelipase suspension) samples are presented in Table 10 below.

TABLE 9

|  | Treated Positive Control | Ct | Mean Ct | HEV (IU/ml) | Intact HEV Expected (Nominal) IU/ml | Intact Hev Expected (actual) IU/ml | Recovery vs nominal spiked conc (%) | Recovery vs actual spiked conc (%) |
|---|---|---|---|---|---|---|---|---|
| Trial A Day 1 | Treated positive control 1 (w centrifugation) | No Ct No Ct |  |  |  |  |  |  |
|  | Treated positive control 1 (wo centrifugation) | No Ct No Ct |  |  |  |  |  |  |
|  | Treated positive control 2 (w centrifugation) | 31.032 31.207 | 31.12 | 48277 | 25275 | 43724 | 191 | 110 |
|  | Treated positive control 2 (wo centrifugation) | 31.000 31.000 | 31.00 | 45391 | 25275 | 43724 | 180 | 104 |
| Trial B Day 2 | Treated positive control 1 (w centrifugation) | No Ct No Ct |  |  |  |  |  |  |
|  | Treated positive control 1 (wo centrifugation) | No Ct No Ct |  |  |  |  |  |  |
|  | Treated positive control 2 (w centrifugation) | 31.849 31.745 | 31.80 | 24996 | 25275 | 43724 | 99 | 57 |
|  | Treated positive control 2 (wo centrifugation) | 31.040 30.786 | 30.91 | 47140 | 25275 | 43724 | 187 | 108 |

TABLE 10

| Treated Pancreatin (Pancrelipase suspension) | | Ct | Mean Ct | Mean HEV (IU/ml) | Intact HEV Expected Nominal (IU/ml) | Intact HEV Expected Actual (IU/ml) | Recovery on Nominal % | Recovery on Actual % |
|---|---|---|---|---|---|---|---|---|
| Trial A Day 1 | Treated pancreatin 1 (w centrifugation) | No Ct No Ct | | | | | | |
| | Treated pancreatin 1 (wo centrifugation) | No Ct No Ct | | | | | | |
| | Treated pancreatin 2 (w centrifugation) | 38.308 36.589 | 37.45 | 911 | 25275 | 43724 | 4 | 2 |
| | Treated pancreatin 2 (wo centrifugation) | 35.392 35.080 | 35.24 | 3650 | 25275 | 43724 | 14 | 8 |
| Trial B Day 2 | Treated pancreatin 1 (w centrifugation) | No Ct No Ct | | | | | | |
| | Treated pancreatin 1 (wo centrifugation) | No Ct No Ct | | | | | | |
| | Treated pancreatin 2 (w centrifugation) | 36.670 36.624 | 36.65 | 770 | 25275 | 43724 | 3 | 2 |
| | Treated pancreatin 2 (wo centrifugation) | 35.189 35.483 | 35.34 | 1972 | 25275 | 43724 | 8 | 5 |

Example 5

Controlled Digestion and Filtration of Encapsidated and Free HEV RNA Samples

Controlled digestion of encapsidated and free HEV RNA samples are carried out with and without filtration. Molecular filters are used to remove cellular contaminants smaller than 300 kDa that could interfere with RNA extraction. Sample is prepared by spiking 0.7 ml of RNase free water containing 50 µg DNase/ml and 0.5 U RNase/ml with 80 µl of 250,000 IU/ml intact or naked HEV. The solution is allowed to be digested by the RNase and DNase for about 1 hour at room temperature and 15.6 µl DTT at a concentration of 1M is added to the solution to inhibit the RNase and DNase degradation reaction. The solution is further incubated for about 1 hour at 37° C. 500 µl of the sample are then diluted 1:10 with $H_2O$+Tween 20 0.05% and centrifuged at 10.000×g for 10 minutes. The supernatant is applied to the top of 300 kDa molecular filter and centrifuged at room temperature at 1800×g until 1 ml is obtained on top of the filter. 4 ml of $H_2O$+Tween 20 0.05% are added to the top solution and the centrifugation is repeated after 180° rotation of the filter and until 0.5 ml of sample is present on top. Viral RNA is extracted from this sample and quantified. 140 µl of non-filtrated samples are used as controls.

Results of filtered samples and non-filtered controls are reported in Table 11. In samples spiked with intact virus the recovery is very low for filtrated samples, while non-filtration controls showed 100% recovery compared to the actual measured input and ~200% vs the nominal concentration. The filtration step appears to be detrimental to the protocol, with high HEV RNA losses. As for naked RNA spiking, negligible viral RNA was detected after extraction and quantification in samples with/without the filtration step.

TABLE 11

| Sample | Ct | Mean Ct | HEV (IU/ml) | HEV Expected actual (IU/ml) | HEV Expected nominal (IU/ml) | Recovery vs actual spiked conc (%) | Recovery vs nominal spiked conc (%) |
|---|---|---|---|---|---|---|---|
| Intact (encapsidated) HEV RNA with filtration (1) | 32.782 32.802 | 32.79 | 3,727.67 | 44,356 | 25,640 | 8.4 | 14.5 |
| Intact (encapsidated) HEV RNA with filtration (2) | 33.907 33.737 | 33.82 | 1,754.97 | 44,356 | 25,640 | 4.0 | 6.8 |
| Intact (encapsidated) HEV RNA without filtration (1) | 31.092 31.018 | 31.06 | 47,573.25 | 44,356 | 25,640 | 107.3 | 185.6 |
| Intact (encapsidated) HEV RNA without filtration (2) | 30.987 31.017 | 31.00 | 49,447.43 | 44,356 | 25,640 | 111.5 | 192.9 |
| Free (naked) HEV RNA with filtration (1) | 37.397 36.824 | 37.11 | 160.69 | 32,426 | NA | 0.5 | NA |
| Free (naked) HEV RNA with filtration (2) | 36.56 38.633 | 37.60 | 143.41 | 32,426 | NA | 0.4 | NA |
| Free (naked) HEV RNA without filtration (1) | 37.198 37.535 | 37.37 | 468.81 | 32,426 | NA | 1.4 | NA |
| Free (naked) HEV RNA without filtration (2) | 36.366 37.628 | 37.00 | 676.65 | 32,426 | NA | 2.1 | NA |

NA: Not Applicable

The method described herein is effective at digesting large quantities of naked (free) viral RNA present in the samples. The method described and exemplified herein is effective for the detection of HEV post API manufacture or drug production. The method described herein reduces the incidence of false positives resulting from the presence of contaminating RNA fragments in the samples. Lack of RNase activity post extraction indicated removal of substantially all degraded nucleic acid for detection of intact (encapsidated) HEV virus RNA present in the pancrelipase.

The present invention is not limited to the embodiments described and exemplified above, but is capable of variation and modification within the scope of the appended claims.

We claim:

1. A method for detecting Hepatitis E virus contamination in a sample comprising pancrelipase, the method comprising (a) treating the sample with a ribonuclease to catalyze degradation of substantially all free RNA in the sample comprising pancrelipase, (b) treating the sample with a ribonuclease inhibitor, (c) treating the sample with an agent to denature capsid of Hepatitis E virus, and (d) amplifying with PCR and detecting encapsidated Hepatitis E virus RNA, wherein the method reduces false positive results of Hepatitis E viral contamination in the sample.

2. The method of claim 1, optionally comprising extracting the encapsidated Hepatitis E virus RNA and amplifying the extracted Hepatitis E virus RNA.

3. The method of claim 1, further comprising treating the pancrelipase with a protease inhibitor.

4. The method of claim 1, wherein the ribonuclease is ribonuclease A.

5. The method of claim 1, wherein the sample of step a) further comprises free RNA and encapsidated Hepatitis E virus.

6. The method of claim 1, wherein the ribonuclease inhibitor comprises 1,4-dithiothreitol (DTT).

7. The method of claim 1, wherein b) further comprises heating pancrelipase and removing a cellular debris via centrifugation or molecular filters.

* * * * *